(12) United States Patent
Blaine

(10) Patent No.: US 10,386,310 B2
(45) Date of Patent: Aug. 20, 2019

(54) SYSTEM FOR MEASURING LEVELS OF RADIATION REFLECTING FROM SEMICONDUCTOR MATERIAL FOR USE IN MEASURING THE DOPANT CONTENT THEREOF

(71) Applicant: Aurora Solar Technologies (Canada) Inc., North Vancouver (CA)

(72) Inventor: Stephen Warren Blaine, West Vancouver (CA)

(73) Assignee: Aurora Solar Technologies (Canada) Inc., North Vancouver (CA)

( * ) Notice: Subject to any disclaimer, the term of this patent is extended or adjusted under 35 U.S.C. 154(b) by 0 days.

(21) Appl. No.: 15/507,545

(22) PCT Filed: Aug. 28, 2015

(86) PCT No.: PCT/CA2015/050829
§ 371 (c)(1),
(2) Date: Feb. 28, 2017

(87) PCT Pub. No.: WO2016/209321
PCT Pub. Date: Mar. 3, 2016

(65) Prior Publication Data
US 2017/0248528 A1      Aug. 31, 2017

Related U.S. Application Data

(60) Provisional application No. 62/044,026, filed on Aug. 29, 2014.

(51) Int. Cl.
*G01J 3/433*      (2006.01)
*G01N 21/95*      (2006.01)
(Continued)

(52) U.S. Cl.
CPC ........ *G01N 21/9501* (2013.01); *G01J 3/0254* (2013.01); *G01J 3/433* (2013.01);
(Continued)

(58) Field of Classification Search
CPC .... G01N 21/9501; G01N 21/55; H01L 22/12; H01L 31/18; G01J 3/0254; G01J 3/433
See application file for complete search history.

(56) References Cited

U.S. PATENT DOCUMENTS

| | | | |
|---|---|---|---|
| 4,458,152 A | 7/1984 | Bonora | |
| 4,602,160 A | 7/1986 | Mactaggart | |

(Continued)

FOREIGN PATENT DOCUMENTS

| | | |
|---|---|---|
| CA | 1027234 A | 2/1978 |
| CN | 103047998 A | 4/2013 |

(Continued)

OTHER PUBLICATIONS

Stumpf Investigation and Simulation of the Optical Properties of Doped Silicon (Dec. 2001 Universitat Konstanz Thesis), 56 pages, [retrieved on Jul. 6, 2018]. Retrieved from the Internet:< URL: http://nbn-resolving.de/urn:nbn:de:bsz:352-opus-11979>.*

(Continued)

*Primary Examiner* — David P Porta
*Assistant Examiner* — Shun Lee
(74) *Attorney, Agent, or Firm* — Norton Rose Fulbright Canada LLP

(57) ABSTRACT

A system and method of non-contact measurement of the dopant content of semiconductor material by reflecting infrared (IR) radiation off of the material into an integrating sphere to scatter the received radiation and passing portions of the radiation through band pass filters of differing wavelength ranges, comparing the level of energy passed through each filter and calculating the dopant content by referencing (Continued)

a correlation curve made up of known wafer dopant content for that system.

24 Claims, 17 Drawing Sheets

(51) Int. Cl.
*H01L 31/18* (2006.01)
*G01J 3/02* (2006.01)
*G01N 21/55* (2014.01)
*H01L 21/66* (2006.01)
*G01N 21/3563* (2014.01)

(52) U.S. Cl.
CPC ......... *G01N 21/3563* (2013.01); *G01N 21/55* (2013.01); *G01N 21/9505* (2013.01); *H01L 22/12* (2013.01); *H01L 31/18* (2013.01); *G01N 2021/3568* (2013.01); *G01N 2201/062* (2013.01); *G01N 2201/065* (2013.01); *G01N 2201/06113* (2013.01)

(56) References Cited

U.S. PATENT DOCUMENTS

| | | | |
|---|---|---|---|
| 4,830,486 | A | 5/1989 | Goodwin |
| 4,900,923 | A * | 2/1990 | Gerlinger ............ G01N 21/474 250/228 |
| 5,430,386 | A | 7/1995 | Morin et al. |
| 6,815,236 | B2 | 11/2004 | Kim et al. |
| 7,236,243 | B2 | 6/2007 | Beecroft et al. |
| 7,410,815 | B2 | 8/2008 | Vagos |
| 7,504,838 | B1 | 3/2009 | Zhao et al. |
| 8,299,416 | B2 | 10/2012 | Arbore et al. |
| 8,314,628 | B2 | 11/2012 | Clarysse et al. |
| 8,823,406 | B2 | 9/2014 | Bolt et al. |
| 8,829,442 | B2 | 9/2014 | Heaven et al. |
| 8,896,837 | B1 * | 11/2014 | Ranish ............... G01N 21/55 356/445 |
| 8,927,944 | B2 | 1/2015 | Solarz |
| 2004/0119984 | A1 | 6/2004 | Andreev et al. |
| 2013/0043393 | A1 | 2/2013 | Heaven et al. |

FOREIGN PATENT DOCUMENTS

| | | |
|---|---|---|
| CN | 2030053454 U | 7/2013 |
| CN | 103308499 A | 9/2013 |
| CN | 102435582 B | 12/2013 |
| WO | 00/54031 WO | 9/2000 |

OTHER PUBLICATIONS

Labsphere Technical Guide Integrating sphere theory and applications, Dec. 2013, 22 pages, [retrieved on Jul. 6, 2018]. Retrieved from the Internet:< URL: https://web.archive.org/web/20131217221742/http://www.labsphere.com/uploads/technical-guides/a-guide-to-integrating-sphere-theory-and-applications.pdf>.*

Gigahertz-Optik P-9801 Optometer Brochure (Jan. 2014), 4 pages, [retrieved on Jul. 6, 2018]. Retrieved from the Internet:< URL: https://web.archive.org/web/20140114050009/http://www.light-measurement.com:80/pdf-files/P-9801.pdf>.*

Baker-Finch, Simeon C. et al., "Near-infrared free carrier absorption in heavily doped silicon", Journal of Applied Physics, American Institute of Physics, US, vol. 116, No. 6, Aug. 14, 2014.

Extended European Search Report for European patent application No. EP 15836614, European Patent Office, dated Jan. 11, 2018.

Schroeder, Dieter K., Surface Voltage and surface photovoltage: history, theory and applications, Meas. Sci. Technol. 12 (2001) R16-R31.

Ruland, E. et al., Comparative Study on Emitter Sheet Resistivity Measurements For Inline Quality Control, Proceedings of 3rd World Conference on Photovoltaic Energy Conversion, May 11-18, 2003, Osaka, Japan, p. 1085-1087.

Isenberg, J. et al., Fast, Contactless and Spatially Resolved Measurement of Sheet Resistance by an Infrared Method, Prog. Photovolt: Res. Appl. 2004; 12:539-552.

International Search Report and Written Opinion for international application No. PCT/CA2015/050829, International Searching Authority, dated Nov. 3, 2015.

Supplementary Partial European Search Report for European patent application No. EP 15836614, European Patent Office, dated Sep. 28, 2017.

* cited by examiner

SYSTEM FOR MEASURING LEVELS OF RADIATION REFLECTING FROM SEMICONDUCTOR MATERIAL FOR USE IN MEASURING THE DOPANT CONTENT THEREOF

CROSS REFERENCE TO RELATED APPLICATIONS

This is the US national stage of International Application No. PCT/CA2015/050829, filed on Aug. 28, 2015, which in turn claims the benefit of U.S. provisional patent application No. 62/044,026 filed Aug. 29, 2014. Both U.S. provisional patent application No. 62/044,026 and International Application No. PCT/CA2015/050829 are hereby incorporated herein by reference in their entirety.

FIELD OF THE INVENTION

This invention relates generally to the measurement of the dopant content in one or more layers of a semiconductor device and to systems and methods of non-contact measurement of the dopant content of such devices in an associated commercial fabrication line, such as for photovoltaic (PV) solar cells, LEDs and any other semiconductor devices employing diffused, implanted or epitaxially deposited doped layers.

More specifically the invention relates to methods and systems for measuring levels of radiation reflected from semiconductor material for use in measuring the dopant content thereof by directing the source radiation at the semiconductor material at a suitable angle and collecting reflected radiation with an integrating sphere, as a part of the measurement system previously described in issued U.S. Pat. No. 8,829,442, as modified herein. An alternative embodiment for an un-collimated infrared radiation source provides a collimator (which can be a conduit or light pipe), for directing the source radiation at the suitable angle.

BACKGROUND

As background, we will describe both the crystalline silicon (c-Si) PV cell fabrication process and the semiconductor LED fabrication process.

To make a c-Si PV cell, a silicon wafer is subjected to a series of processing steps in a cell fabrication line. Each incoming wafer is lightly bulk-doped (i.e. diffused throughout) with atoms that creates "free carriers" (in semiconductor parlance) that are either donors (creating an n-type wafer) or acceptors (creating a p-type wafer). The first step (after incoming inspection to discard defective wafers or to sort the wafers into lots) is to run the wafers through a wet chemical etching process to remove saw marks and other surface defects and contamination. Each wafer is then isotropically textured (another wet process) to microscopically roughen its surface, enhancing its ability to capture incident photons. After texturing, the wafer is then doped with a chemical that creates "free carriers" (in semiconductor parlance), of the opposite type to the bulk doping, in a very thin layer extending from the surface(s) of the wafer. In current practice, this doping may occur in one of two methods—an "in-line" method or a "batch" method. The in-line method deposits the dopant chemical on the top surface of the wafer, usually carried in a liquid form. (In the case of a phosphorus dopant, this carrier is most commonly phosphoric acid). The deposited dopant carrier is then dried and the resultant product is then diffused (using a high-temperature furnace) into each wafer to form a semiconductor junction that will allow the wafer to produce electricity when exposed to sunlight. In this in-line method the wafers are conveyed continuously through the equipment performing these steps, which typically consist of first a "doper" machine to apply the liquid carrier, then a "dryer" machine to dry the carrier, leaving the dopant chemical on the surface, and a third machine, an in-line diffusion furnace which diffuses the dopant into the wafer. In the batch method, the wafers are loaded into a cassette (most commonly made of quartz and called a "boat" in semiconductor parlance) which is inserted into a "tube" diffusion furnace, which is then sealed, and the wafers are simultaneously exposed to the dopant carrier in gaseous form (most commonly phosphoryl chloride) and heated to diffuse the dopant into the wafers. The wafers are then removed from the furnace, unloaded from the boat and moved to the next part of the fabrication line. In both methods, the amount of dopant introduced, the time spent in the diffusing process and the temperature of the diffusing process determine the penetration depth and concentration by depth of the second dopant. Also, the second dopant is, by nature of the diffusing process introduced and diffused into all of the surfaces of the wafer. Note: from this point onward, "dopant" refers to this second dopant introduced on the surface(s) of the bulk-doped wafer, unless specifically referenced. Each wafer is then wet-etched again to remove phospho- or boro-silicate glass (also called PSG or BSG, a by-product of the dopant diffusing step) and may be etched to pattern or remove all or a portion of the dopant on the "back" side to prevent shunting. Following this step, a coating (most commonly silicon nitride) is applied to the top surface of the wafer to reduce reflections and passivate the surface. This coating is usually applied using plasma-enhanced chemical vapour deposition equipment. After this, the wafer has metal contacts printed on its top and bottom surfaces, with the top contact pattern designed to minimally interfere with the light exposure to the Si material while providing a path of minimal electrical resistance to the flow of current out of the wafer. These metal contacts (which are printed in the form of a metallic paste) are dried and then diffused into the wafer using a furnace. After this, if the portion of the dopant that is on the back of the wafer has not been previously fully or partially removed, a laser or mechanical device is used to cut a groove around the outside perimeter of the wafer to prevent shunting. Finally, the wafer (which is now a finished PV cell) is tested and graded.

Dopant concentrations, as a function of their distribution within the volume of the wafer, plays a central role in determining the quantum efficiency and other electrical characteristics of the resulting finished PV cell, which ultimately result in its power output capacity and market value. Therefore, the steps within the PV cell fabrication process that are concerned with the quantity and distribution of the dopants that are diffused into the wafer are a focus. Specifically, these steps are: (a) the initial "base" doping of the raw wafer, as supplied by the wafer manufacturer (in most cases at the present time, the raw wafers are positively doped using boron); and (b) the later doping of the outside regions of the wafer (in most cases at the present time this is negative doping using phosphorous). The second doping step forms what is known as the "emitter". We will use the term "base" to refer to the raw wafer doping, and the term "emitter" to refer to the resulting semiconductor formation produced by the second doping step.

In order to ensure that the emitter formation process is within the required specifications, certain measurements are taken that provide an indication of the raw wafer base dopant concentration and the emitter dopant concentration. In current practice, photovoltaic (PV) wafers are often inspected manually or by single-point visual measurement devices that use visible-spectrum industrial cameras at varying intervals in the PV cell fabrication process. Except for the raw material acceptance stage (at the beginning of the fabrication line) and the final inspection and grading (at the end of the fabrication line), continuous in-line measurement of wafers is often limited in scope and coverage, and off-line non-continuous sampling is used instead, particularly for inspection of properties not amenable to interrogation by visible-spectrum industrial camera technology. When off-line sampling is used, in the time interval between samples, hundreds of wafers can pass through the step or steps of interest in the fabrication process. This situation is common at the process steps that determine the application, concentration and distribution of dopants within the PV wafers, and therefore these steps are not well controlled at present, limiting the yield of acceptable finished goods in PV cell manufacturing plants. To raise yields, the industry is now seeking to implement continuous in-line measurements, ideally on 100 percent of the wafers, in order to better control the steps that affect dopant concentration and distribution in the PV wafers.

A semiconductor Light Emitting Diode (henceforth referred to simply as an "LED") performs the opposite function to a PV cell. Instead of absorbing photons to generate electricity, an LED uses electricity to emit photons (a phenomenon called electroluminescence). In LED fabrication the wafers are composed of a neutral substrate such as sapphire. As compared to PV cell fabrication, the wafers are polished rather than textured, each wafer contains multiple LEDs, and the dopants used to create the semiconductor are deposited as epitaxial layers on the surface of the wafer, rather than diffused by the diffusion process used in PV cell manufacturing. Notwithstanding these structural and fabrication differences, these dopant layers may be examined by the same method disclosed in this invention. From this point forward, for simplicity and clarity, PV cell structure will be described without limiting the application of the invention to other doped semiconductor structures.

In PV cell fabrication, a number of existing and novel techniques have been proposed for in-line measurement of emitter doping, but all have serious limitations. For measurement of the diffused dopants, they are Surface Photo-voltage (SPV) measurement of diffusion length, eddy current measurement of sheet resistance, and an infrared method for measurement of sheet resistance measurement developed at Germany's Fraunhofer Institute for Solar Energy Research. (J. Isenberg, D. Biro and W. Warta, "Fast, Contactless and Spatially Resolved Measurement of Sheet Resistance by an Infrared Method", Prog. Photovolt: Res. Appl. 2004; 12:539-552). To our knowledge, no method exists for measurement of a wet dopant carrier film.

SPV measurements have been used in the lab for measuring diffusion length (how long an excess carrier in a bulk semiconductor travels, on average, before recombining to achieve equilibrium carrier concentration). See for example: D. K. Schroder, "Surface voltage and surface photovoltage: history, theory and applications", Meas. Sci. Technol. 12 R16-R31, 2001. SPV measurement is typically performed by placing a wafer on a ground electrode (although a non-contact method without a rear sensor plate is possible) and positioning a capacitive probe a small distance above the sample. Because the measurement is capacitive, the measurement area is very limited, the maximum stand-off distance is extremely small and there is little tolerance for wafer bow or vertical movement. Also, in conveyor-fed manufacturing operations, because of the limited stand-off distance there is a significant opportunity for "crashes" causing a jam on the conveyor if any wafers are stuck together (a not uncommon situation), if a wafer breaks and the pieces are not flat on the conveyor (again not uncommon), or if any foreign objects are inadvertently introduced to the conveyor, or if the conveyor itself experiences a small vertical oscillation exceeding the sensor stand-off distance. Finally, because of the requirement for specialized wafer conveyance, and the very close standoff distance requirement for SPV measurement, introduction of such technology into an existing fabrication line may require significant line modifications that can render its usage costly and impractical.

Eddy current measurement has many of the same limitations as SPV and has previously been shown to be unsuitable for in-line measurement of emitter doping (using sheet resistance measurement as the metric). (Rueland, E.; Fath, P.; Pavelka, T.; Pap, A.; Peter, K.; Mizsei, J, "Comparative study on emitter sheet resistivity measurements for inline quality control", Photovoltaic Energy Conversion, 2003. Proceedings of 3rd World Conference on Volume 2, Issue, 12-16 May 2003 Page(s): 1085-1087 Vol. 2.)

The Fraunhofer method, while suitable for the laboratory, has many requirements that make it unsuitable for practical in-line use, most notably the stringent requirement for absence of spurious heat or light that is extremely difficult and expensive to provide in an in-line fabrication environment.

There is consequently a need for a method and apparatus that is flexible, configurable, robust and cost-effective for the purpose of in-line measurement of raw wafer dopant concentration, of the amount and distribution of a wet dopant film emerging from an in-line doper, and of the dopant concentration in an emitter at any step in the manufacturing line following diffusion.

There is further a need for defining specific, repeatable sample sites for each wafer in order to be able to map intra-wafer emitter variations, whether intentional or not. As a corollary, there is also a need for an apparatus and method with the ability to vary the scanning "intensity" (the number of samples taken per unit length in the cross-machine direction over a certain time period), in order to allow the operator to perform periodic or unscheduled in-depth measurement, if necessary.

There is also a need for a system for consistently capturing receiving radiation reflected from the wafer surface despite surface roughness and variability in scattering patterns over different regions of the wafer. And there is further a need to direct that radiation substantially equally between the two detectors. And there is further a need to direct the incident radiation on the wafer from the radiation source in a manner that minimises the effect of specular reflection.

SUMMARY OF THE INVENTION

In an embodiment of the invention, a system for measuring levels of radiation reflected from semiconductor material for use in measuring the dopant content of the material includes: a) an infrared radiation source; b) a modulator for modulating the radiation from the infrared radiation source; c) an integrating sphere having a first opening for receiving the modulated radiation from the source and a second opening for receiving radiation reflected from the material, the sphere configured to scatter the received radiation reflected from the material within the sphere; d) a collimator configured to direct the radiation from the infrared radiation source through the sphere to impact the material at an angle from the normal with reference to the material, the angle sufficient to minimise radiation from being reflected directly back to the collimator and also to minimise radiation entering the sphere before reflection from the semiconductor material; e) a first baffle positioned within the sphere to prevent the received radiation reflected from the material from travelling to the first band pass filter without first scattering within the sphere; f) a second baffle positioned within the sphere to prevent the received radiation reflected from the material from travelling to the second band pass filter without first scattering within the sphere; g) a first band pass or edge pass filter positioned to receive a first portion of the received radiation reflected from the material, the first band pass or edge pass filter configured to pass a limited wavelength band of infrared radiation from within the overall spectrum emitted by the infrared radiation source through the first filter; h) a second band pass or edge pass filter positioned to receive a second portion of the received radiation reflected from the material, the second band pass or edge pass filter configured to pass a limited wavelength band of infrared radiation from within the overall spectrum emitted by the infrared radiation source through the second filter, wherein the limited wavelength band that is passed by the second filter is different as compared to the limited wavelength band passed by the first filter; i) a first radiation detector positioned to receive the radiation that passes the first filter and configured to determine a first level of energy; and j) a second radiation detector positioned to receive the radiation that passes the second filter and configured to determine a second level of energy.

In an alternate embodiment the angle from the normal may be about ten degrees. In another embodiment the collimator may comprise a conduit extending at least partially within the sphere. In a further embodiment the conduit may be a light pipe. In another embodiment the light pipe may extend lengthwise through the centre of the sphere for substantially the entire diameter of the sphere. In another embodiment the collimator may comprise a lens configured to focus the modulated radiation from the source to travel through the sphere to impact the material. In a further embodiment the modulated radiation from the source may exit the sphere to impact the material through the second opening.

In another embodiment the first and second baffles may be configured to block substantially the same degree of received radiation reflected from the material. The collimator may be positioned to collimate the radiation from the source prior to impacting the material.

The sphere may comprise an internal surface configured to enhance reflection within the sphere of the received radiation reflected from the material. The conduit may comprise an outer surface configured to enhance reflection of the radiation within the sphere of the received radiation reflected from the material.

In various embodiments: The second opening may be positioned a distance from the material to cause substantially all of the radiation reflected from the material to enter the sphere irrespective of surface variations of the material. The second opening may be positioned about 5 mm from the material. The second opening and the downstream opening of the conduit may be in co-axial alignment. The diameter of the second opening of the sphere may be larger than the diameter of the downstream opening of the conduit. The modulator may be selected from the group: a) a modulator using high speed chopping wheel; b) a modulator using pulse modulation of the source; and c) a modulator using frequency modulation of the source. The radiation source may be either: a) a multi-wavelength infrared laser, b) more than one infrared laser each at a different wavelength, c) one or more infrared light emitting diodes, or d) a source of broadband infrared radiation. The pass-band for both the first and second filters may be longer than 1 micrometer, and the pass band for the first filter is different than the pass-band for the second filter. The light pipe may comprise an outer surface configured to enhance reflection in the sphere of the received radiation reflected from the material. The second opening of the sphere may be about 3 cm in diameter and the sphere may be about 5 cm in its inner diameter. The diameter of the conduit downstream opening is about 1.3 cm. The ratio of the second opening diameter to the inner diameter of the sphere may be about 3 to 5. The ratio of the second opening diameter to the diameter of the light pipe downstream opening may be about 2 to 1. An amplifier may be included in the system for amplifying the determinations of first and second levels of energy, the amplifier synchronized to the radiation modulation frequency.

In a further alternate embodiment a system for measuring levels of radiation reflected from semiconductor material for use in measuring the dopant content of the material includes: a) a source of collimated infrared radiation; b) a modulator for modulating the radiation from the infrared radiation source; c) an integrating sphere having a first opening for receiving the modulated radiation from the source and a second opening for receiving radiation reflected from the material, the sphere configured to scatter the received radiation reflected from the material within the sphere; d) a first baffle positioned within the sphere to prevent the received radiation reflected from the material from travelling to the first band pass filter without first scattering within the sphere; e) a second baffle positioned within the sphere to prevent the received radiation reflected from the material from travelling to the second band pass filter without first scattering within the sphere; f) a first band pass or edge pass filter positioned to receive a first portion of the received radiation reflected from the material, the first filter configured to pass a limited wavelength band of infrared radiation from within the overall spectrum emitted by the infrared radiation source through the first filter; g) a second band pass or edge pass filter positioned to receive a second portion of the received radiation reflected from the material, the second band pass filter configured to pass a limited wavelength band of infrared radiation from within the overall spectrum emitted by the infrared radiation source through the second filter, wherein the limited wavelength band that is passed by the second filter is different as compared to the limited wavelength band passed by the first filter; h) a first radiation detector positioned to receive the radiation that passes the first band pass filter and configured to determine a first level of energy; and i) a second radiation detector positioned to receive the radiation that passes the second filter and configured to determine a second level of energy; wherein the source of collimated infrared radiation is configured to direct the radiation through the sphere to impact the material at an angle from the normal with reference to the material, the angle sufficient to minimise radiation from being reflected directly back to the collimator and also to minimise radiation entering the sphere before reflection from the semiconductor material.

In general, Applicant has developed an improved system comprising a different optical path design as compared to applicant's system which is the subject of its issued U.S. Pat. No. 8,829,442 (sometimes referred to herein as the earlier embodiment(s)). A goal for this improved system was to make the doping concentration measurement less sensitive to the variation of the wafer's surface characteristics. The new design is also more compact.

DETAILED DESCRIPTION

The basic technology and technique remain the same as in the earlier embodiments of FIGS. 1-9. Applicant has developed improvements to how the system delivers the energy to the wafer and collects the reflections for the detectors, as described in a preferred embodiment with reference to FIGS. 10-17.

General Particulars:

The same types of infrared radiation source is used;

The same types of modulator for that source is used;

No parabolic reflector or lenses of any kind to deliver the infrared energy to the wafer is used in the embodiments having a collimator. In an embodiment, a light pipe (which may be gold plated) is used to deliver the modulated infrared energy to the wafer surface;

No lens is used to collect the reflected energy from the wafer;

An integrating sphere is used to collect the reflected energy from the wafer. The sphere is positioned close to the wafer (approximately 5 mm), to more consistently capture a much larger percentage of the reflected energy as compared to a lens at the larger standoff distance of the earlier embodiment;

Two detectors, each with a different infrared filter (which may be a band pass or edge pass filter) in front of the detectors, is used to receive portions of the radiation. These detectors are now mounted directly to the integrating sphere;

Baffles are positioned within the integrating sphere to avoid a direct optical path from the wafer to either detector;

The light pipe used to deliver the energy to the wafer in an embodiment is co-axially mounted in the integrating sphere and is offset from a normal angle to the wafer to minimize specular reflection back into the light pipe;

There is no reliance on reflected energy from any of the band pass or edge pass filters and no beam splitters are used;

The processing of the detector signals remains the same as in the earlier embodiment. However, in addition to using the difference or ratio of outputs from the two detectors to determine the dopant level, a formula or look-up table that uses any combination of these two signals—either analytically or experimentally determined to suffice—may be used.

A doped silicon (or indeed any semiconductor) wafer has a characteristic absorption, reflection amplitude and reflection phase/polarization of infrared radiation corresponding to the spatial concentration of free charge carriers due to the doping. In particular, n-doped silicon exhibits significantly different free carrier absorptions (or as a corollary, reflectance) of infrared spectra at different doping levels, as shown in FIG. 1 and FIG. 2.

Figure 1:
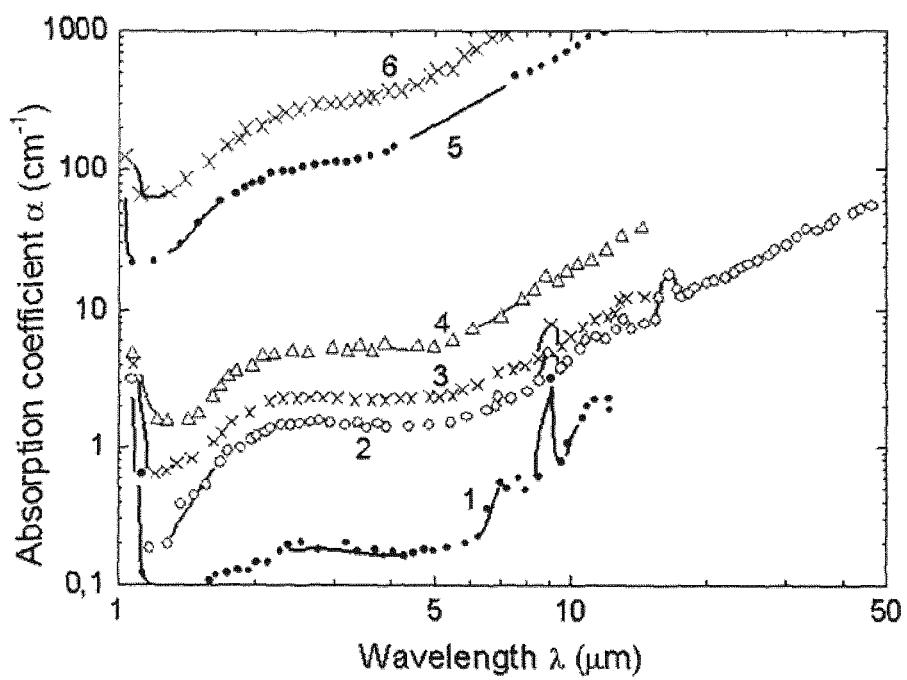
FIG. 1 is a graph of free carrier absorption vs. wavelength at different doping levels (n-Si)

FIG. 1 is a graph of free carrier absorption vs. wavelength for varying negative dopants diffused at different concentrations, forming a negatively doped silicon substrate (n-Si) at 300° K. With reference to the numbers on the graphs of FIG. 1, the dopant concentrations (in atoms per cubic centimeter) are: $1-1.4\times10^{16}$ cm$^{-3}$ (arsenic dopant); $2-8\times10^{16}$ cm$^{-3}$ (antimony); $3-1.7\times10^{17}$ cm$^{-3}$ (antimony); $4-3.2\times10^{17}$ cm$^{-3}$ (phosphorus); $5-6.1\times10^{18}$ cm$^{-3}$ (arsenic tin alloy); and $6-1\times10^{19}$ cm$^{-3}$ (arsenic).

Figure 2:
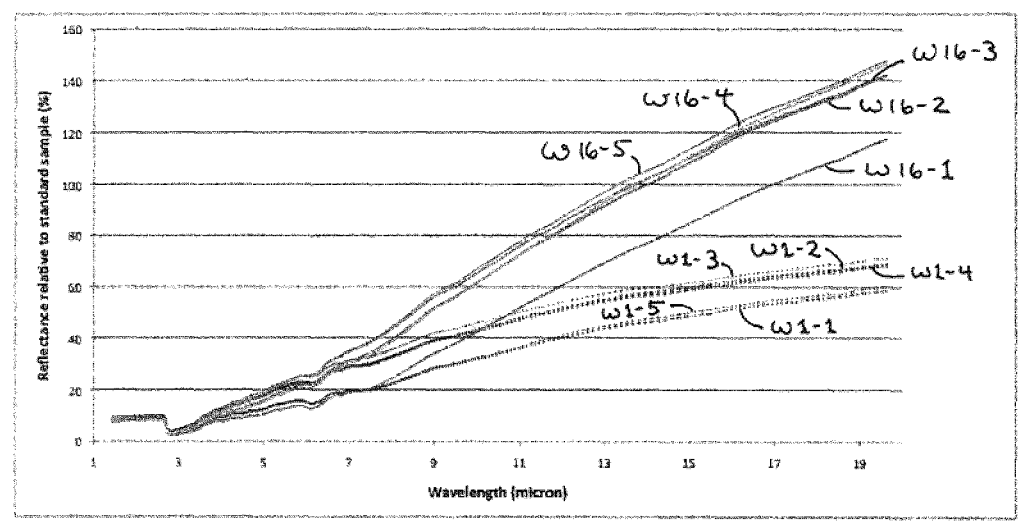
FIG. 2 is a graph of differentiated reflectance of undoped (W1) and doped (W16) c-Si wafers.

FIG. 2 is a graph of differentiated reflectance by infrared wavelength of a two polycrystalline (poly c-Si) wafers—one bulk-doped with boron only (W1) and another with also a phosphorus layer diffused into its top surface (W16). The numerals 1-5 following W1 and W16 identify segments on each wafer that were examined. The measurements on the graph are normalized with respect to a pure crystalline silicon reference sample. The graph demonstrates that as the incident infrared wavelength lengthens, the corresponding reflectance of the wafer with the phosphorus-doped layer, as compared to the reference sample, is distinctively stronger compared to the bulk-doped wafers, therefore indicating that the added dopant layer is influencing the reflectance as a function of infrared wavelength and as a corollary, the normalized slope of the infrared reflectance versus wavelength can be used to determine the doping level of this layer.

Additionally, the presence of any chemical layer or film, not just phosphorus, and whether diffused or not, upon a dissimilar substrate causes refractions, reflections, wavelength shifts and phase changes that can be used to determine the layer/film thickness and/or conditions at the boundary. The magnitude, phase, polarization and wavelengths of such absorption and reflections are dependent upon the particular films or dopant(s) used, the density and thickness of the film or doping, and the nature of any underlying substrate.

By transmitting infrared radiation at known wavelengths and intensity levels on a wafer or substrate, the absorption of the characteristic wavelengths can be measured as a function of the reflected values observed at the receiver. Phase shifts, wavelength changes, and polarization changes may also be measured. Since the amount of energy absorbed varies in proportion to the amount and composition of the wet film, or to the emitter doping concentration, as the case may be, the wet film concentration, depth and distribution, or the emitter density, respectively, can be measured by measuring the difference between irradiated and reflected energy.

It is desirable to take measurements or samples from multiple, specific locations on the wafer or substrate. This is both because single samples can exhibit wide variance and it may be necessary to smooth these variances, and also because the wafer or substrate may have purposely-differentiated deposition of a wet film or diffusion of a dopant.

Also, for each sample, by using simultaneous differential interrogation at the sample site, the apparatus and method described herein can tolerate light, heat and vibrations from the factory environment and compensate for temperature, varying standoff distances and varying angles of incidence.

Figure 3:
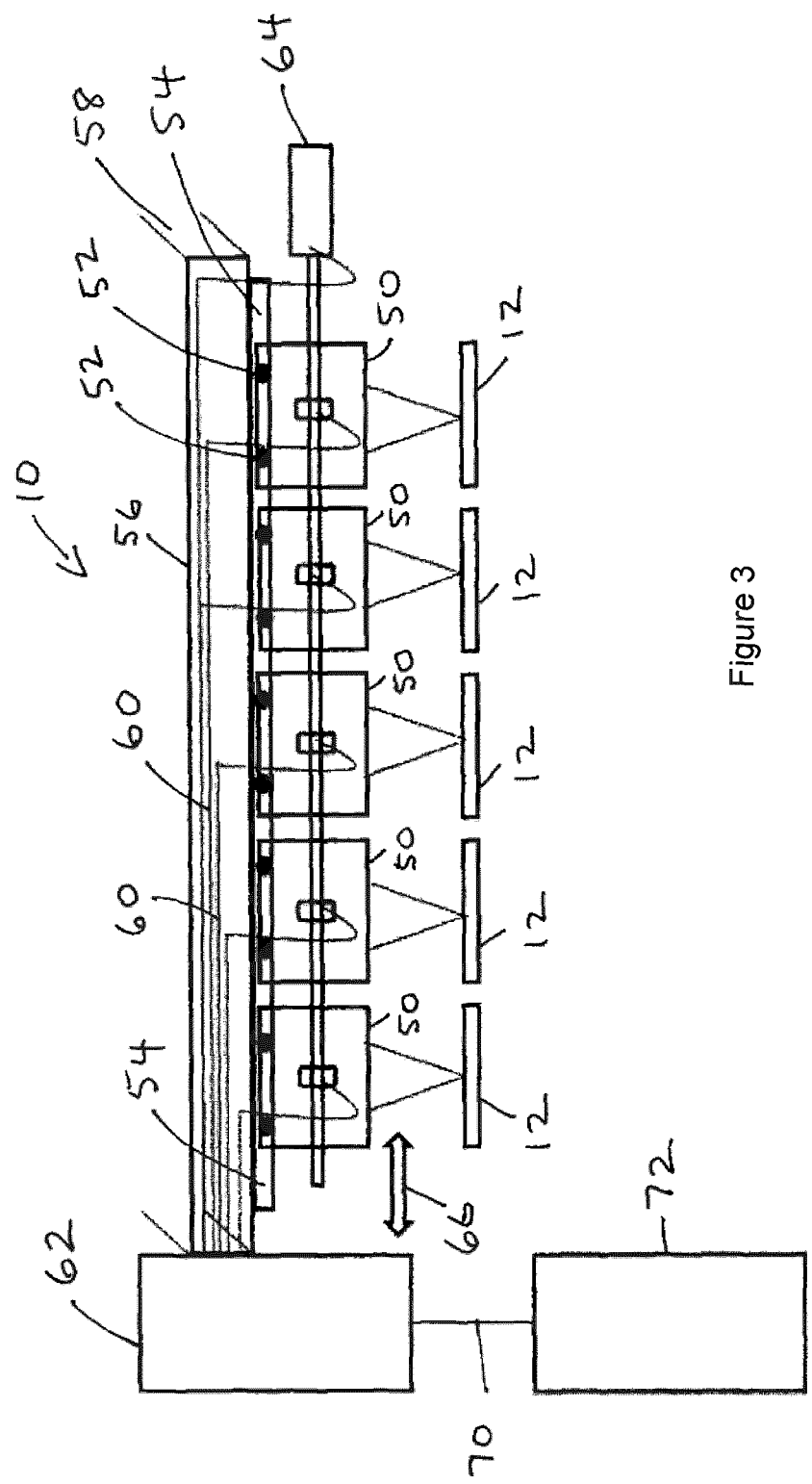
FIG. 3 is a schematic block diagram of a non-contact system for measuring the dopant content of semiconductor material in accordance with an embodiment of the disclosure.

The apparatus 10 described in FIG. 3 is for a multi-lane, conveyor-fed, photovoltaic ("PV") cell fabrication facility. Although it should be understood that single-lane and/or non-conveyor configurations are also possible, including for LED and other semiconductor fabrication facilities.

One or more transmitters and receivers are mounted over the area where the PV wafer 12 is to be measured. Each receiver consists of two or more sensors—the purpose being to capture differential signal data as explained above. For simplicity and clarity, a non-contact system for measuring the dopant content of doped silicon will be described in respect of an apparatus 14 consisting of a single transmitter 16 and a single receiver 18, the latter consisting of two sensors 20, 22. This is illustrated with reference to FIG. 4, which depicts schematically an alternate embodiment of the disclosure as a block diagram.

A sensor housing containing the equipment in the block diagram is located approximately 50-150 millimeters above the wafer 12 surface.

There are at least four possible embodiments of the transmitter, each containing a different source of infrared radiation. In the first embodiment the source is composed of one or more continuous broadband infrared source(s) mounted in an elliptical reflector. In the second embodiment, the source is composed of one or more infrared LEDs. In the third embodiment, the source is composed of a multi-wavelength infrared laser. In the fourth embodiment the source is composed of two single-wavelength infrared lasers.

In the disclosure in issued U.S. Pat. No. 8,829,442, and referring to the first embodiment of the transmitter, in FIG. 4 the elliptical reflector 24 of the infrared source 16 focuses the wide spectrum of infrared radiation from the infrared source to a single point in space. A chopper wheel 26 is located at the focal point of the ellipse which modulates the infrared radiation at approximately 1 kHz, although the radiation may be modulated by any appropriate method, or combination of methods, including amplitude, frequency, pulse, or phase shift modulation. The use of modulation is necessary as the detectors respond to changes in detected signals and because the modulation differentiates the transmitted infrared signal from background infrared radiation and enhances the signal to noise ratio. The modulation can also be used to generate information about the dopant content by measuring its effect on the modulation via the changes induced in the reflected signals.

An off axis elliptical reflector 28 is shown facing the infrared source 16 to receive the modulated radiation. The elliptical reflector 28 focuses the modulated radiation from the chopper wheel 26 onto a measurement point 30 on the wafer 12 at an incidence of approximately 45 degrees to the wafer 12 and aligns the peak of the radiation in the center of the first lens 32 of the receiver 18 (discussed below). Although it will be appreciated that the reflector 28 is not necessary in the second and third embodiments of the transmitter 16 as the lasers are already in collinear format.

There are at least two possible embodiments of each receiver 18. In the first embodiment of the receiver 18, the receiver 18 is mounted above the measurement point 30 where the infrared radiation strikes the wafer 12. The reflected infrared radiation is diffuse and is collected by the first lens 32 and directed to a first limited band-pass filter 34. The first filter passes a limited band of infrared radiation centered at a selected wavelength of the infrared spectrum. This wavelength is selected such that effects of the isotropic texturing on the received signal properties of interest are not significant. The other portion of the received radiation is reflected by the first filter 34.

The reflected radiation is directed onto a second limited band-pass filter 36 centered at a different selected wavelength such that the wavelengths of the two bands do not overlap. Similarly this second wavelength is selected such that any effect of the isotropic texturing on the received signal properties of interest are not significant. In a preferred embodiment, one band pass filter 34 or 36 has the central band-pass at approximately 8 micrometers with a pass-band of +/−125 nanometers and the other filter 34 or 36 has the central band-pass at approximately 10.5 micrometers with a pass-band of +/−175 nanometers.

In a further preferred embodiment in the disclosure in issued U.S. Pat. No. 8,829,442 the pass-band of each band pass filter is between 50 nanometers and 500 nanometers. And in another preferred embodiment the center of the pass-band for one filter is between 1 and 20 micrometers. In another preferred embodiment the center wavelength of the pass-band for the second filter is between 1 and 20 micrometers and different than the center wavelength of the pass-band of the first filter.

In a further preferred embodiment in the disclosure in issued U.S. Pat. No. 8,829,442 the difference between the center wavelengths of the first and second filters is between 1 and 10 micrometers. And in a further preferred embodiment the difference between the center wavelengths of the first and second filters is 2 micrometers.

In another preferred embodiment in the disclosure in issued U.S. Pat. No. 8,829,442 the center wavelength of the first filter is set at 8.06 micrometers and the center wavelength of the second filter is set to 10.5 micrometers with each filter having a pass-band width of between 200 and 400 nanometers.

The radiation that passes the first filter 34 is focused by a second lens 38 onto a first infrared detector or sensor 20 which produces a low voltage signal in proportion to the intensity of the infrared radiation that reaches the first detector 20. The radiation that passes the second filter 36 is focussed by a third lens 40 onto a second infrared detector or sensor 22 which produces a low voltage signal in proportion to the intensity of the infrared radiation that reaches the second detector 22.

The low voltage signal of each detector 20, 22 is amplified by respective amplifiers 42, 44 and then acquired by an analog-to-digital data acquisition board 46 synchronized to the chopper frequency in the transmitter 16 and controlled by a computer 48. Thus the sensors 20, 22 produce two voltage values, proportional to the infrared energy in two limited bands passing respective first and second filters 34, 36.

The computer 48 uses the voltage from each detector 20, 22 to calculate the slope and/or the ratio between the amount of energy received in each band which, as has been shown above, is proportional to the energy absorbed by the dopant in the top layer of the wafer 12. The dopant content is determined by computation or table look-up based on models of infrared reflections of the wafer material at varying dopant content, in particular (but not limited to) passing the slopes though a correlation curve, as exemplified in FIG. 9.

In a second embodiment of the receiver in the disclosure in issued U.S. Pat. No. 8,829,442, a beam splitter is used to split the reflected IR energy at the focal point of the first lens into equal parts and direct the resultant equal parts onto an array of detectors, each with a different band-pass filter in front of the detector. Each detector delivers a voltage in proportion to the intensity of infrared radiation reaching each detector. Thus, multiple points on the doping to wavelength correlation curve are measured, improving the accuracy of the slope measurement (because the slope can vary by wavelength) and therefore the dopant content in or on the semiconductor material.

In a further embodiment of apparatus 14 instead of band pass filter 34 positioned behind lens 32 a beam splitter is positioned behind lens 32. This separates the beam from lens 32 into two beams which are directed to respective band pass filters 34, 36, respective lenses 38, 40 and then respective sensors 20, 22.

Figure 4:
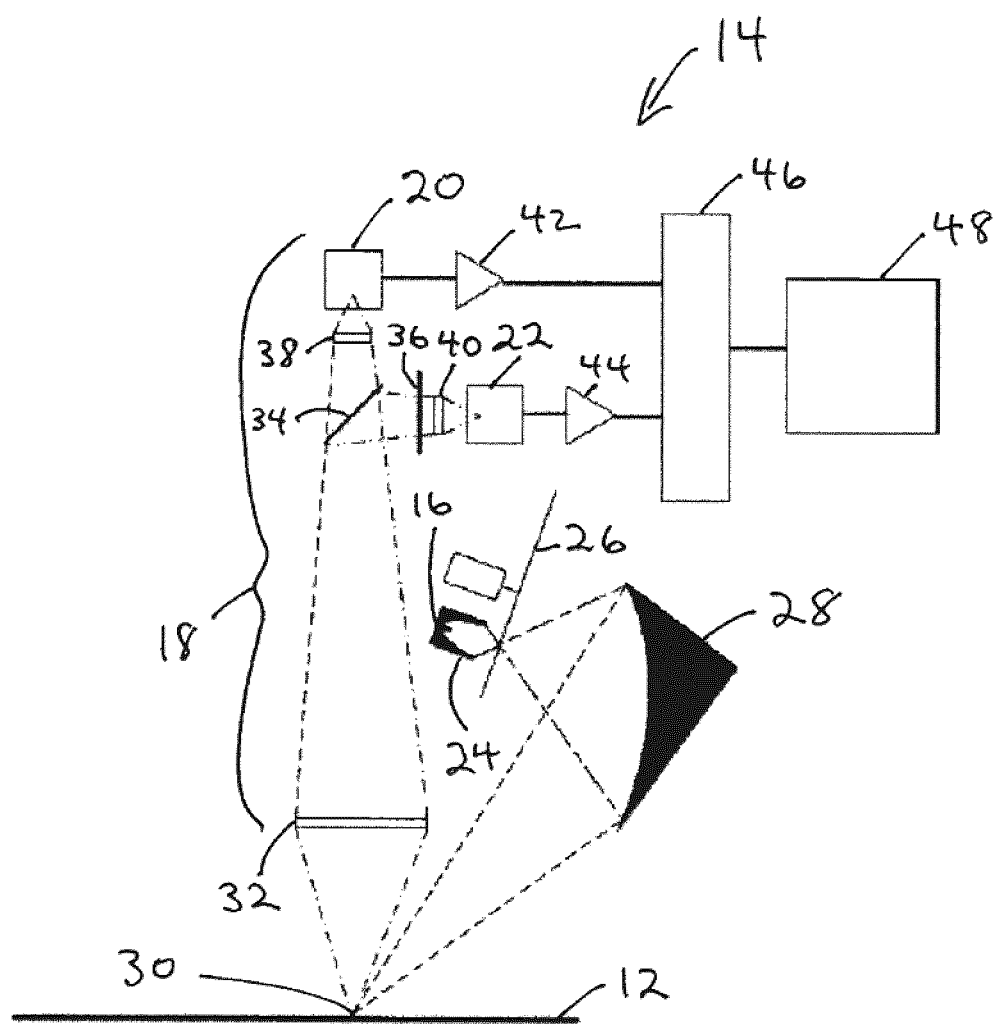
FIG. 4 is a schematic block diagram of a non-contact system for measuring the dopant content of semiconductor material in accordance with an embodiment of the disclosure in issued U.S. Pat. No. 8,829,442, consisting of a single transmitter and a single receiver, the latter consisting of two sensors.

The subject surface, shown in FIG. 4 as a single semiconductor wafer 12, can also be multiple semiconductor wafers on a conveyor, stationary wafers, or a monolithic surface such as a thin film on a substrate. The surface(s) can be of any size.

In the disclosure in issued U.S. Pat. No. 8,829,442, a preferred embodiment of a non-contact system for measuring the dopant content of semiconductor material 10 is shown in FIG. 3 in the form of a schematic block diagram. A plurality of sensor heads 50 are mounted between 5 millimeters and 250 millimeters above a wafer conveyor (not shown) in alignment perpendicular to the direction of travel of the conveyor. Each sensor head 50 includes a housing into which the components of the apparatus of FIG. 4 are contained, including a single transmitter 16 and single receiver 18 (from FIG. 4). The receiver 18 incorporates the two sensors 20, 22 (FIG. 4). Furthermore those components are configured to operate in the manner discussed above with reference to FIG. 4. In particular, inside each sensor head is the infrared source 16, chopper wheel 26, focusing reflector 28, lens 32 to collect reflected infrared radiation and to direct the infrared radiation onto a band pass filter 34 or beam splitter, two detectors 20, 22 that produce a voltage in proportion to the amount of infrared radiation in a given frequency range and a means of amplifying 42, 44 and converting 46 this voltage into a digital signal at a frequency synchronized with gaps in the chopper wheel 26.

Each sensor head 50 rides on wheels 52 in a precise track 54 perpendicular to the direction of travel of the conveyor. The track 54 is supported by the support beam 56 which is fixed to the equipment frame 58 or alternatively, supported from the floor. Power to each sensor head is delivered by corresponding power cables 60 from the power and terminations cabinet 62. The power cables 60 are configured so that the heads 50 are free to move along the track 54 over a defined measurement range. The array of sensor heads 50 is moved along the track 54 together in the directions of arrow 66 by a linear actuator 64 which positions each head 50 over a corresponding wafer 12 below, riding on the conveyor. The combination of conveyor and linear actuator 64 movement allows a pattern to be measured across the wafers.

Figure 5:
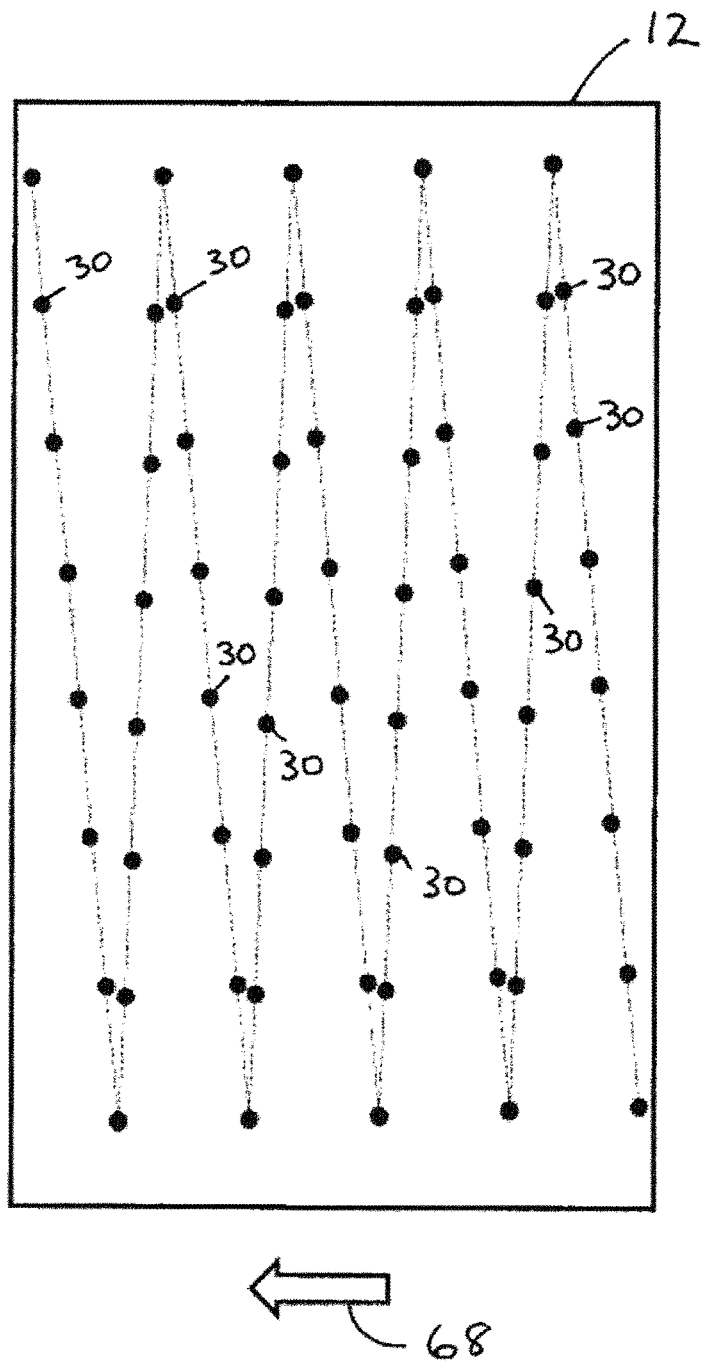
FIG. 5 is a schematic top view of methods of sampling at various test locations of a wafer and sampling patterns in accordance with an embodiment of the disclosure.

When in use, the linear actuator 64 and conveyor move in directions at right angles to each other. This causes the pattern of measurement points 30 to be diagonal in nature, as depicted in FIG. 5. The conveyor moves in the direction of arrow 68. However, if the actuator 64 is moved much faster than the conveyor, it is possible to measure each wafer 12 at several points across the wafer 12. This is exemplified by the pattern of measurement points 30 shown by dots in FIG. 5 some of which are as marked with reference numeral 30. It can be seen from FIG. 5 that when the linear actuator 64 moves in the reverse direction a further diagonal pattern of measurement points 30 can be made. This can be repeated multiple times as the wafer 12 is moved by the conveyor in the direction of arrow 68. The array of measurement points 30 and their location across the wafer 12 for a constant conveyor speed is a function of the sampling rate and the speed of the linear actuator 64.

At each measurement point 30, the amplified voltage from the two detectors 20, 22 of the receiver 18 of each sensor head 50 is converted to a digital signal using a multiplexed analog to digital conversion board 46 and embedded computer 48 located in the sensor head 50 (FIG. 4). The resulting values are sent over a fieldbus or LAN cable that can be combined with power cable 60 to the power and termination cabinet 62. The resultant two measurements at each measurement point 30, as well as the position of the measurement point corresponding to the linear actuator 64 position are sent to a computer 72 and stored for each measurement point 30. The presence of the wafer 12 on the conveyor is known based on a step increase in the overall signal level at the sensors 20, 22.

The sample sites and/or sampling rate on a particular wafer 12 or other substrate may be defined to follow a specific pattern. Additionally, a pattern may be pre-defined, and more than one pattern may be pre-defined. Over a series of samples, one or more patterns may be used, or the sample sites (measurement points 30) and sampling rate may be arbitrarily varied. This variable sampling technique is illustrated in FIG. 5. Additionally, the sample sites may be varied in the "direction of travel" by exploiting the movement of the wafers 12 or other substrate on the conveyor.

In order to make the sampling site locations repeatable from wafer 12 to wafer 12, the sites must be offset from a specific two-dimensional location defined on the subject surface. Where the subject surface consists of multiple wafers 12, two edges of each wafer 12 are used as the reference for all the sampling sites on that wafer 12. These edges are located by detecting the radiation level change in the received signal when a wafer 12 is present versus the signal when only the conveyor is present.

Figure 9:
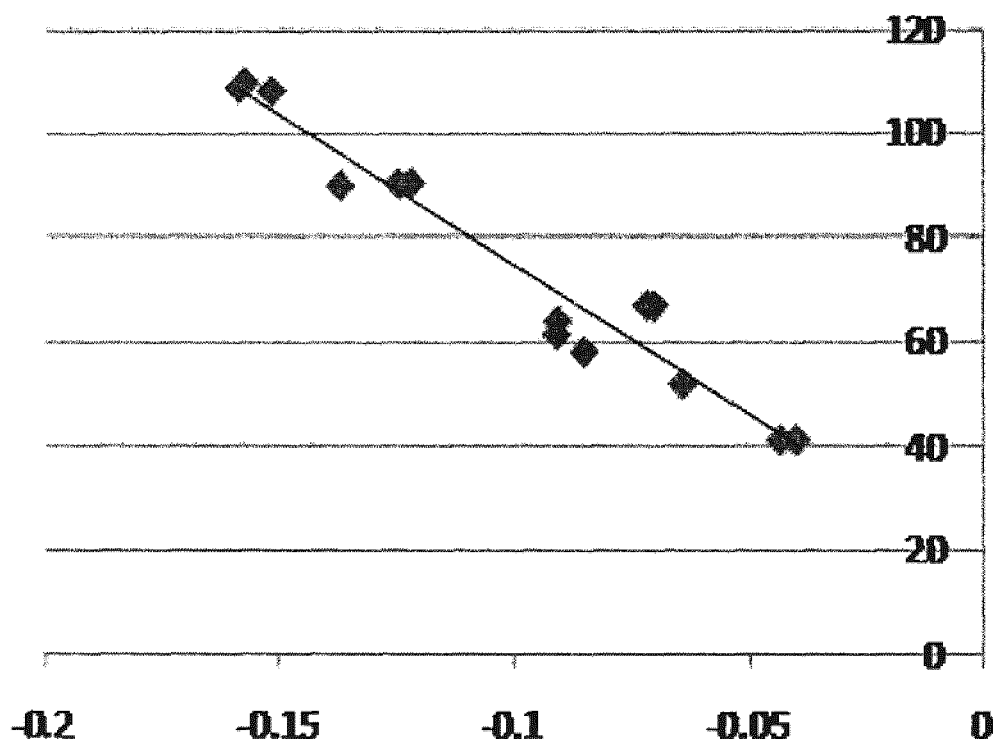
FIG. 9 is a graph of an exemplary diagram showing the correlation of a non-contact system for measuring the dopant content of a layer of semiconductor material to the sheet resistance, as measured by a four-point probe, of said layer of semiconductor material in accordance with embodiments of the disclosure.

The ratio or differences in voltage from each sensor 20, 22 of the receiver 18 in a sensor head 50 is used as the dependent variable in a correlation curve relating this ratio/difference to the independent variable which is the dopant content of the wafer. The correlation curve is determined by passing wafers of known dopant content (measured using a lab-based contacting four point probe or other off-line measurement techniques such as electrochemical capacitance-voltage profiling) under the sensor head 50 and measuring the resulting signals at both sensors 20, 22 and performing a least-squares regression relating the observed ratio/difference in voltage to the known the dopant content from the lab measurement. A correlation curve of the type shown in FIG. 9 is thereby produced and stored in the memory of the computer for reference.

If the wafers 12 are staggered or it is desirable to measure a different pattern on each wafer 12, an alternate embodiment comprises a linear actuator for each sensor head 50 and each head 50 on an independent track. However there is an increase in size of the overall measurement system in the direction of travel of the wafers 12 on the conveyor, in this embodiment.

In the disclosure in issued U.S. Pat. No. 8,829,442, an alternate embodiment of a non-contact system for measuring the dopant content of semiconductor material is shown schematically in FIG. 6. A single transmitter 74 housing a single infrared source of radiation (for example, transmitter or source 16 of FIG. 4) is located on one side of the conveyor (not shown) which holds and transports the wafers 12 as part of a fabrication line such as a PV cell fabrication line. The source can be a broadband source with a focusing lens or a laser with selectable wavelengths. The source can be a continuous broadband infrared source. The focused beam is modulated by a chopping wheel or by electronically modulating the laser onto a steering reflector that directs and focuses the beam of radiation onto a selected point on a wafer. All as previously discussed with reference to FIG. 4.

Figure 6:
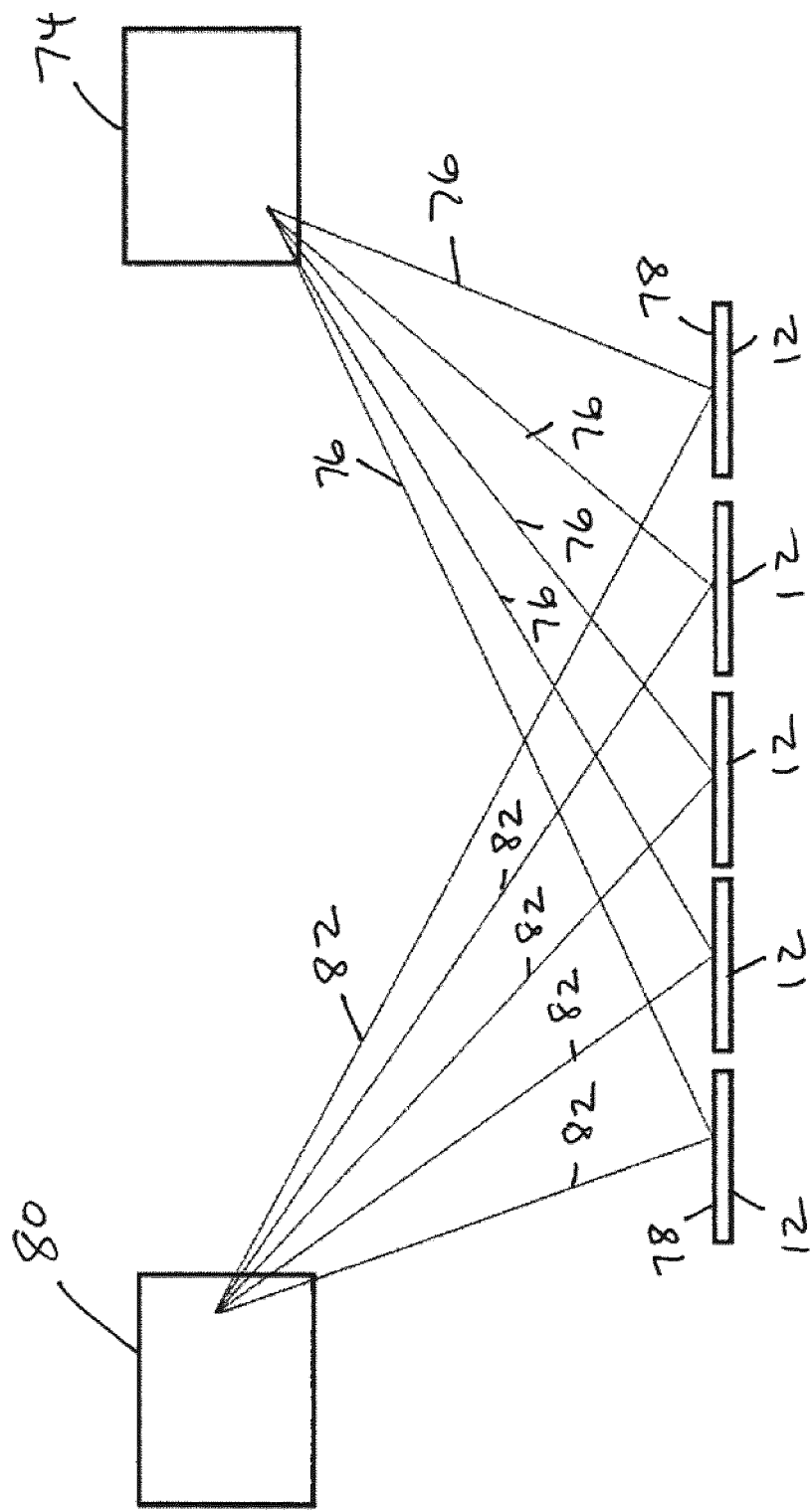
FIG. 6 is a block diagram of a non-contact system for measuring the dopant content of semiconductor material in accordance with an alternate embodiment of the disclosure.

In this embodiment a steering reflector is rotatable about an axis to change the incidence of the transmitted signal 76 to a selected position on the wafer 12 surface 78 at selected intervals in order to direct and focus the beam in series on a group of wafers in a row. While FIG. 6 depicts several transmitted signals 76 and corresponding several received signals 82, it should be understood that the system operates serially and the signals are not generated, nor are they received, concurrently. Similarly if a laser is employed as the source, the steering reflector rotates about an axis to move the beam to contact selected points on the group of wafers 12 moving on the conveyor.

A receiver 80 is positioned on the other side of the conveyor, with a focusing element and a reflector that is adjusted to see the same point on the wafer that is illuminated by the source beam 76. The resulting beam of radiation 82 is directed on by the focusing element on a detector At the time that the transmitter 74 and receiver 80 are oriented to a particular sample site, the transmitter transmits a beam of radiation 76, and the receiver receives such signal 82 as reflected from the wafer surface 78. This transmission and reception occurs over a specific time period, known as the "sample period". (The number of samples taken over a defined time period is known as the "sampling rate"). The shape and size of the observed portion of the wafer 12 surface 78 at the sample site is the "sample area". Within a sample area, there may be a sub-area defined by the shape and size of a particular area that can be seen by the receiver at any time. This is called a sample "spot".

If the source is a broadband source containing a broad spectrum of infrared energy such as a broadband infrared source, it is necessary to split the received signal into two equal parts using a beam splitter as a part of receiver 80 then focus each half on to two narrow-band pass filters, each with a different center wavelength, within receiver 80. The energy that passes each limited band-pass filter is focused on a corresponding one of two detectors, converted to a voltage, amplified and converted to a digital signal corresponding to the energy in each band. The slope or ratio between the two measurements is calculated and stored for the given position of the signal defined by the position of the steering reflector position. This is undertaken in the same manner as discussed above with reference to FIG. 4. The source beam is then moved to a new spot on the wafer and the receiver positioned to see the same spot and the process is repeated for the next location.

If the source is a laser with a selectable wavelength, the laser is alternated between two or more wavelengths and focused on a point using the steerable reflector. The receiver consists of a focusing element and reflector focuses the received energy on a single detector whose voltage is amplified and sampled at the frequency corresponding to the laser modulation frequency.

Figure 7:
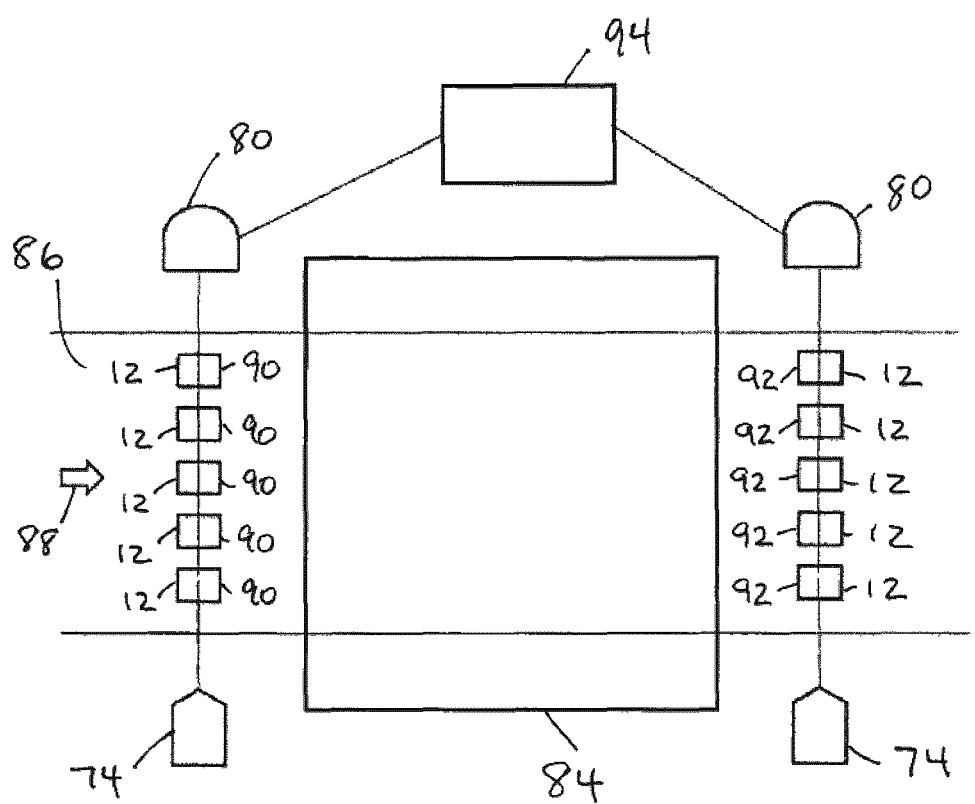
FIG. 7 is a block diagram of a non-contact system for measuring the dopant content of semiconductor material in accordance with an alternate embodiment of the disclosure in which a pair of systems as depicted in FIG. 6 are used on either side of a doping chamber.
Figure 8:
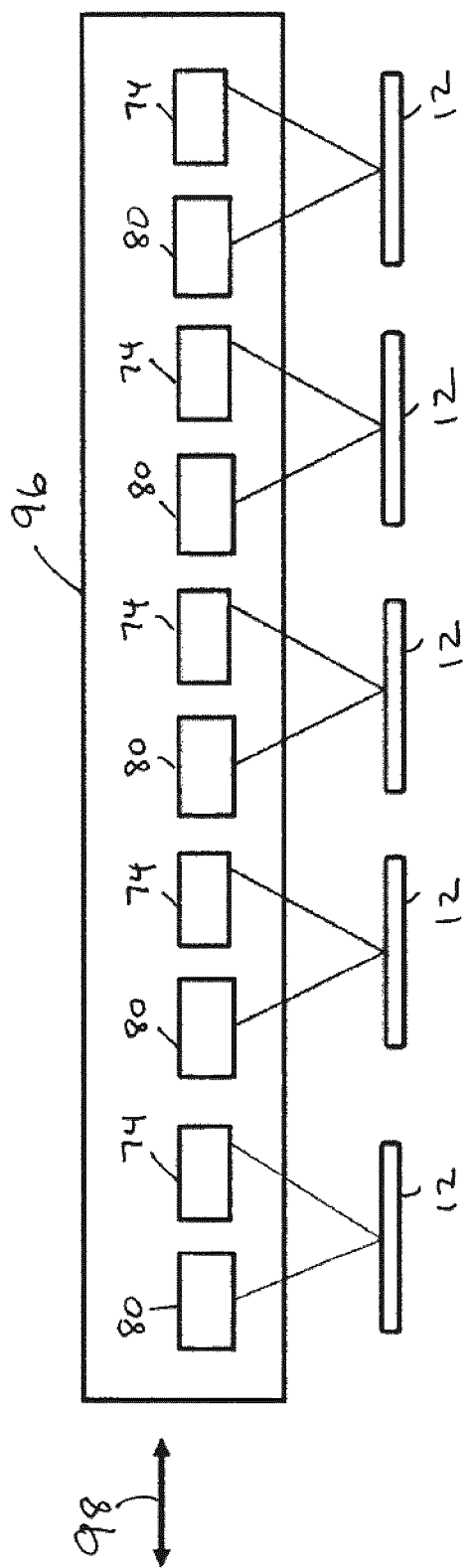
FIG. 8 is a block diagram of a non-contact system for measuring the dopant content of semiconductor material in accordance with an alternate embodiment of the disclosure in which multiple transmitters and receivers are positioned above a series of wafers of semiconductor material.

An alternate embodiment of a non-contact measurement system for measuring dopant content is shown schematically in FIG. 7 for measuring one or more wafers at the beginning of a process step, or a contiguous series of process steps, then measuring the wafer(s) at the end of the process step(s) and calculating the change in infrared reflectance of the wafer(s). This change is used to determine the exact impact of the process on each wafer.

This embodiment may be used in a semiconductor fabrication process wherever dopant or a dopant carrier (such as phosphoric acid) is applied to a wafer surface, dried, or diffused into a wafer, implanted into a wafer, deposited as one or more epitaxial layers, or etched from the surface of a wafer. It may also be used wherever a wafer is treated to create a surface texture.

In this configuration, the wafers 12 ride on conveyor 86 in the direction of arrow 88. The wafers are measured by the system described with reference to FIG. 6 (with numerical references the same in this FIG. 7) before and after the process, or series of processes, carried out by the machine or sequential set of machines (shown as a single entity) 84. This configuration measures the reflectance of the base wafer 90 before the process(es) and then the reflectance of the wafer 92 after the process(es). Computer 94 controls the measurement and comparison process. The system described with reference to FIG. 4 may be used in this system instead of the system described with reference to FIG. 6.

Without limiting the generality of the foregoing, examples of the use of this embodiment for certain PV cell fabrication steps are now described. In the first example, the machine (84) is a doper machine only, and the embodiment is used for measuring the deposited wet dopant carrier on the wafer(s). In the second example, the machine (84) is an in-line diffusion furnace only, and the embodiment is used for measuring the furnace's effect of diffusing into the wafer(s)

the dried dopant that was on the surface of the wafer(s). In the third example, the machine (84) is a diffusion furnace followed by a PSG etch machine, and the embodiment is used for measuring the dopant diffusing and etching process in combination.

In the disclosure in issued U.S. Pat. No. 8,829,442, an alternate embodiment of a non-contact system for measuring the dopant content of semiconductor material is shown schematically in FIG. 8. In this alternate embodiment to the one described with reference to FIG. 3, all the transmitters 74 and receivers 80 (as in FIG. 6) are located in a single supporting structure 96 and the supporting structure 96 is moved together back and forth in the directions of arrow 98 to interrogate the wafers 12 over a pattern as exemplified in FIG. 5.

An example of applicant's method of comparing samples at sensors 20 and 22 is to calculate the difference in the amplitude of the signals received at sensors 20 and 22, divided by the difference between the centre of each of the passbands of the band pass filters 34 and 36, associated with corresponding sensors 20 and 22. On a graph of the reflectance as a function of wavelength, this is the slope of the line intersecting the centre of the passbands of the band pass filters 34 and 36, associated with corresponding sensors 20 and 22. For further clarity, for example, the centre of the passband of band pass filter 34 associated with sensor 20 may be at 8 micrometers, and the centre of the passband of band pass filter 36 associated with sensor 22 might be at 10 micrometers. If the received signal amplitude at sensor 20 is "x" and the received signal value at sensor 22 is "y", then the slope is $(y-x)/2$. Different slopes represent different amounts of the dopant being detected, and by using the slope, the effect of amplitude variations due to the factors described herein are mitigated.

Similar mitigation can be achieved by using the ratio of the signal amplitudes measured at sensors 20 and 22. In this case, the ratio is defined as $y/x$. Likewise, either the difference between, or ratio of, the received signal phases or received signal polarization at sensors 20 and 22 can be used.

FIG. 9 is a graph of an exemplary correlation curve of a non-contact system for measuring the dopant content of semiconductor material in accordance with embodiments of the disclosure. In this example, dopant content is represented as sheet resistance. The curve (in this case a line) of the graph is a correlation between off-line four point probe measurements of sheet resistance (y-axis) and the measurements of the slope of the line between two voltage readings from the two detectors (x-axis). It is generated by placing a series of known and increasingly doped wafers on the conveyor and measuring the resulting voltages from each sensor 20, 22, calculating the resulting slope of the line between the two points (or the ratio of the two voltages) and fitting a linear model using least-squares regression. The observed data points are shown with diamond markings and the best-fit with the line. The $R^2$ value represents the degree to which the calculated line fits the observed measurements and the closer the value is to 1.0, the better the fit of the line to the observed data. In the example of FIG. 9 the $R^2$ value is 0.9486. The line is used to calculate the sheet resistance y corresponding to the observed slope x. For example with reference to FIG. 9: $y=-575.65x+17.391$.

If the slope is $-0.1$, the sheet resistance is: $y=-575.65(0.1)+17.391=74.9$ ohms per square.

A number of samples are taken over a sample area on a wafer or substrate. The values of these samples are collectively processed (for example, but not exclusively, computation of the average value) to provide a meaningful measurement. Each sample area can be well defined and the individual samples do not need to be repeated in exactly the same locations from wafer to wafer or substrate to substrate in order to obtain statistically valid and comparable measurements from wafer to wafer or substrate to substrate.

The pass bands of filters 34 and 36 are chosen to be unequally sensitive to the reflected signal amplitude. By using the comparison between two different values rather than a single absolute measurement, the measurements are normalized to eliminate variations due to any one or more of the following:

Sample-to-sample changes in incident and reflected path lengths and sample area due to scanning across multiple sample sites Sample-to-sample variations in path length, attenuation, or sample area due to vibration or three dimensional position changes in the subject surface (e.g. "bumping" due to conveyor belt irregularities)

Sample-to-sample changes in signal properties due to variations in subject surface texture, crystal boundaries or other surface artifacts such as oxides, phosphosilicate glass, anti-reflective coatings, or contaminants Varying reflectivity due to subject surface temperature variations Varying signal attenuation, phase or polarization due to atmospheric humidity and/or airborne particles Varying ambient light and heat Electrical noise generated within the sensors Wavelength and/or amplitude drift in the transmitted signal, and reference wavelength drift in the receivers Any other source of signal impairment in the measurement environment.

Applicant's invention does not use a modeling system. The invention looks at only specific narrow sections of the reflected spectra using band-pass optical filters and uses the difference or ratio between the energy in these two limited bands to directly infer the free carrier concentration of the semiconductor material. The invention does not use a reference spectrum but instead isolates the energy in two discrete limited bands. The invention uses specific areas of the spectrum found to be sensitive to interaction with the doping layer.

In general, the invention operates by isolating a limited band of infrared radiation reflecting from semiconductor material and measuring the energy in this band compared to another different limited band. Applicant is thereby able to directly infer the amount of dopant in the semiconductor material. Applicant does this by measuring the energy in each band on a set of samples with known doping levels—not by comparing the energy in the full spectrum to a reference spectrum. Applicant takes the energy level difference or ratio as the dependent variable for a given dopant level from each sample as the independent variable, runs a linear regression and is then able to directly deduce the doping level of a new item based on the measured energy level in each limited band.

Systems for Measuring Levels of Radiation Reflecting from Semiconductor Material for Use in Measuring the Dopant Content Thereof Using an Integrating Sphere (FIGS. 10-17)

Figure 10A:
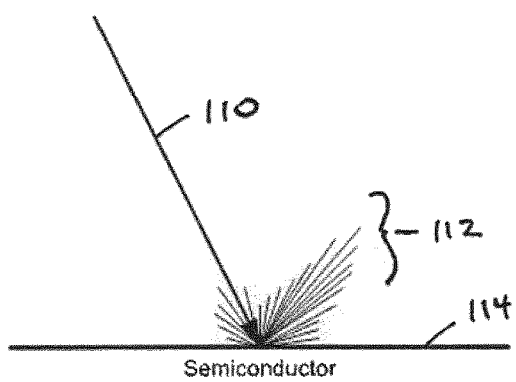
FIGS. 10a and 10b are diagrams showing the different in reflected major energy lobes due to different wafer textures at the point of impact of the source radiation.
Figure 10B:
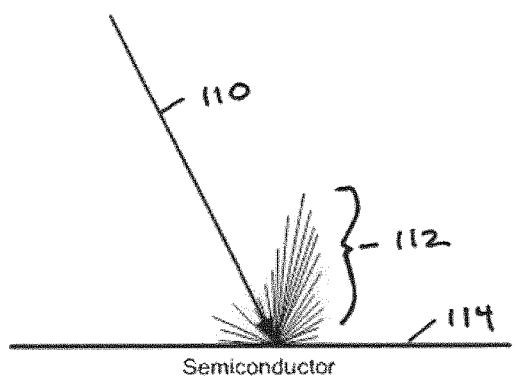

Referring to FIGS. 10a and 10b, an example of two radiation patterns reflected from the semiconductor wafer 114 are shown generally and schematically for illustrative purposes. The source radiation 110 impacts the wafer 114 at the same angle in FIG. 10a as compared to FIG. 10b.

However the pattern 112 of reflected radiation from the wafer 114 differs between the examples in FIGS. 10a and 10b.

The variation in reflected energy scattering illustrated in FIGS. 10a and 10b is due to the fact that the surface roughness (texture and sawmarks) on a semiconductor wafer 114 is generally not uniform if such wafer is roughed to capture light, so the scattering pattern 112 of reflected electromagnetic energy can be different from place to place on the wafer 114. Additionally the variations in surface roughness can also be dissimilar from wafer to wafer. In the earlier embodiments, differing amounts of energy are therefore directed within the detector aperture making the instrument sensitive to wafer surface roughness variations. This interfered with the measurement of the dopant content. The solution was to consistently capture an equal amount of the energy, regardless of the scattering pattern 112 at any given place on the wafer through the use of an integrating sphere to capture the reflected energy. The integrating sphere also facilitates directing the energy to both detectors in a substantially equal manner. However, the integrating sphere's close proximity to the wafer surface creates a physical impediment to applying the source energy onto the wafer, except through the sphere itself. As a solution applicant has developed an embodiment in which the source radiation passes through the sphere. The source radiation is angled from the normal in relation to the wafer. A collimator, which can be a conduit or a light pipe extending through the sphere, or a lens placed after the source, may be used for this purpose. Alternatively, the source may intrinsically provide collimated radiation, such as in the case of using one or more lasers or LEDs for the source. The angling of the source energy is sufficient to minimise radiation from being reflected directly back to the collimator (if present) and also to minimise radiation entering the sphere before reflection from the semiconductor material.

Figure 11:
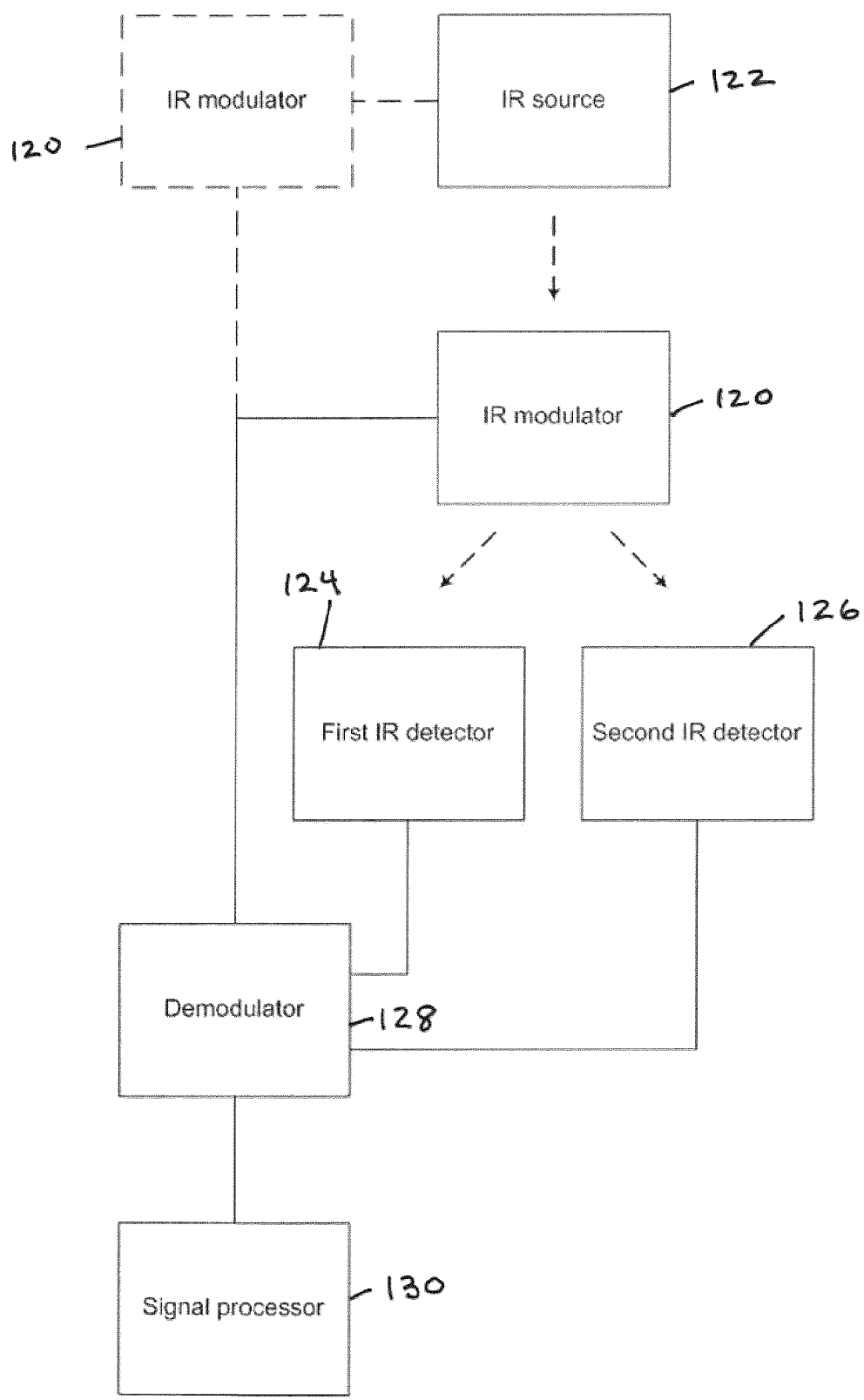
FIG. 11 is a simplified block diagram of several components of a system for measuring levels of radiation reflecting from semiconductor material of the present invention.

FIG. 11 is a simplified block diagram of several components of the system. The IR modulator 120 can be in one of two positions as shown in dashed and solid outline in FIG. 11. In one version the IR modulator 120 is positioned before the IR radiation source 122, and in the other version the IR modulator 120 is positioned after the radiation source 122. The IR modulator 120 when below the radiation source 122 is a wheel with alternate openings and solid areas and spun by motor (not shown in FIG. 11), as discussed below. In the other instance the IR modulator 120 is directly modulating the IR source as shown when placed above the IR source 122 in FIG. 11 as the dashed lines. First and second infrared radiation detectors 124 and 126 are attached to the integrating sphere (not shown in FIG. 11). Radiation reflected from the wafer 114 (FIG. 10) enters the sphere where it is scattered within the sphere. A portion of the radiation, each filtered by band pass filters (not shown), impinges on detectors 124 and 126. Signals from the detectors travel to demodulator 128, which is in synchronisation with modulator 120, for demodulation. The demodulated signal then travels to the signal processor 130 for processing, as discussed more fully above.

Figure 12:
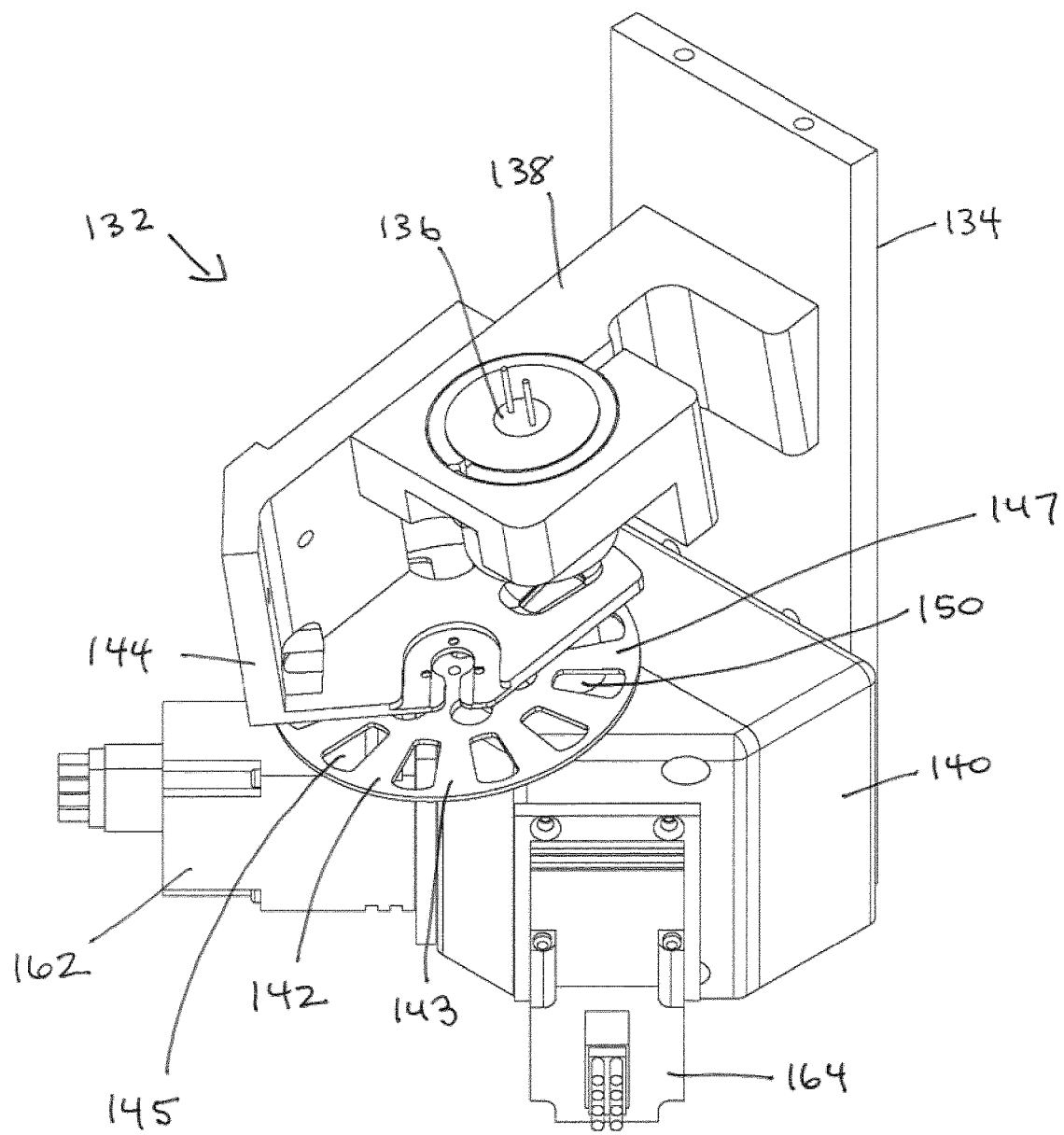
FIG. 12 is a perspective view of the system for measuring levels of radiation reflecting from semiconductor material of the invention of FIGS. 10 and 11.
Figure 13:
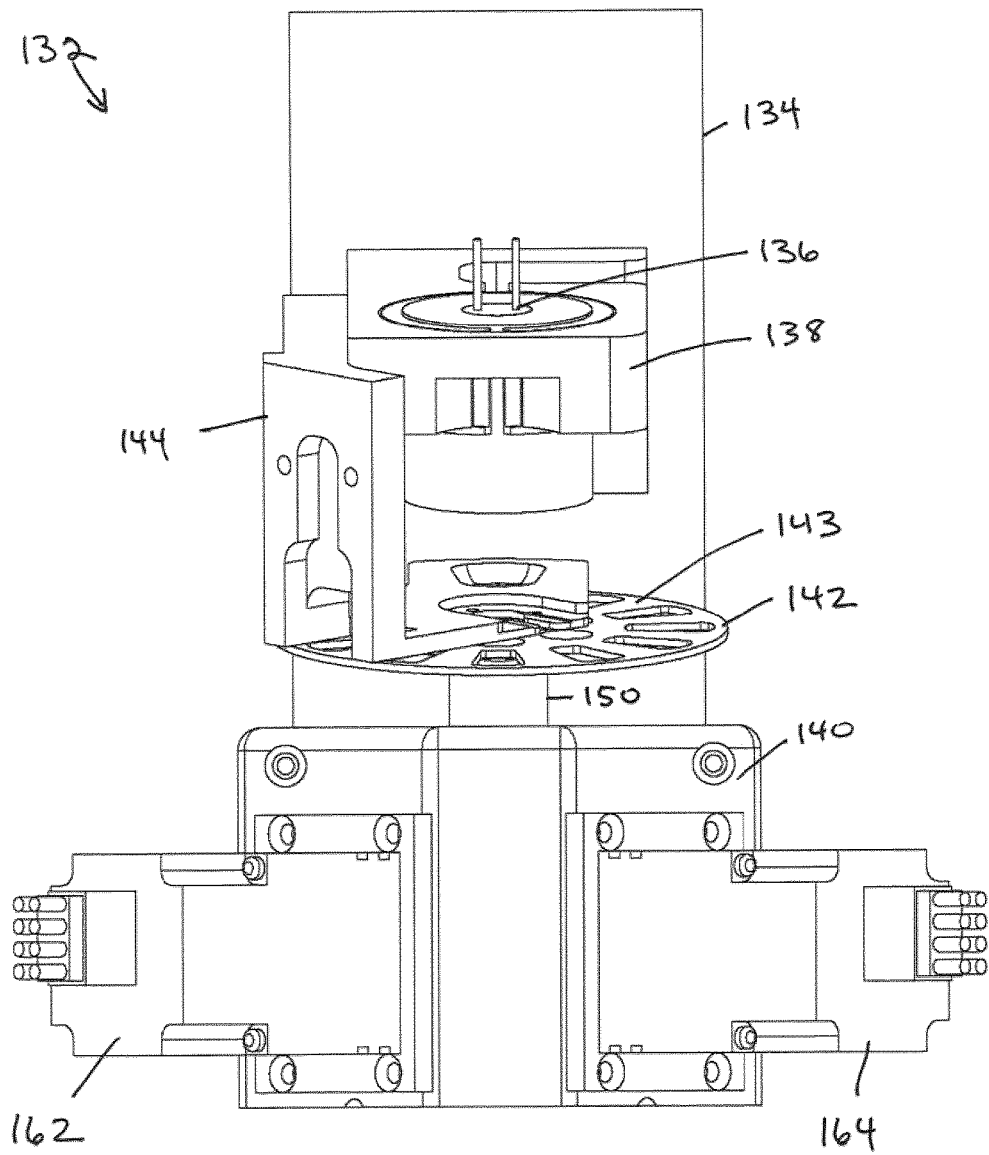
FIG. 13 is front view of the system of FIG. 12.
Figure 14:
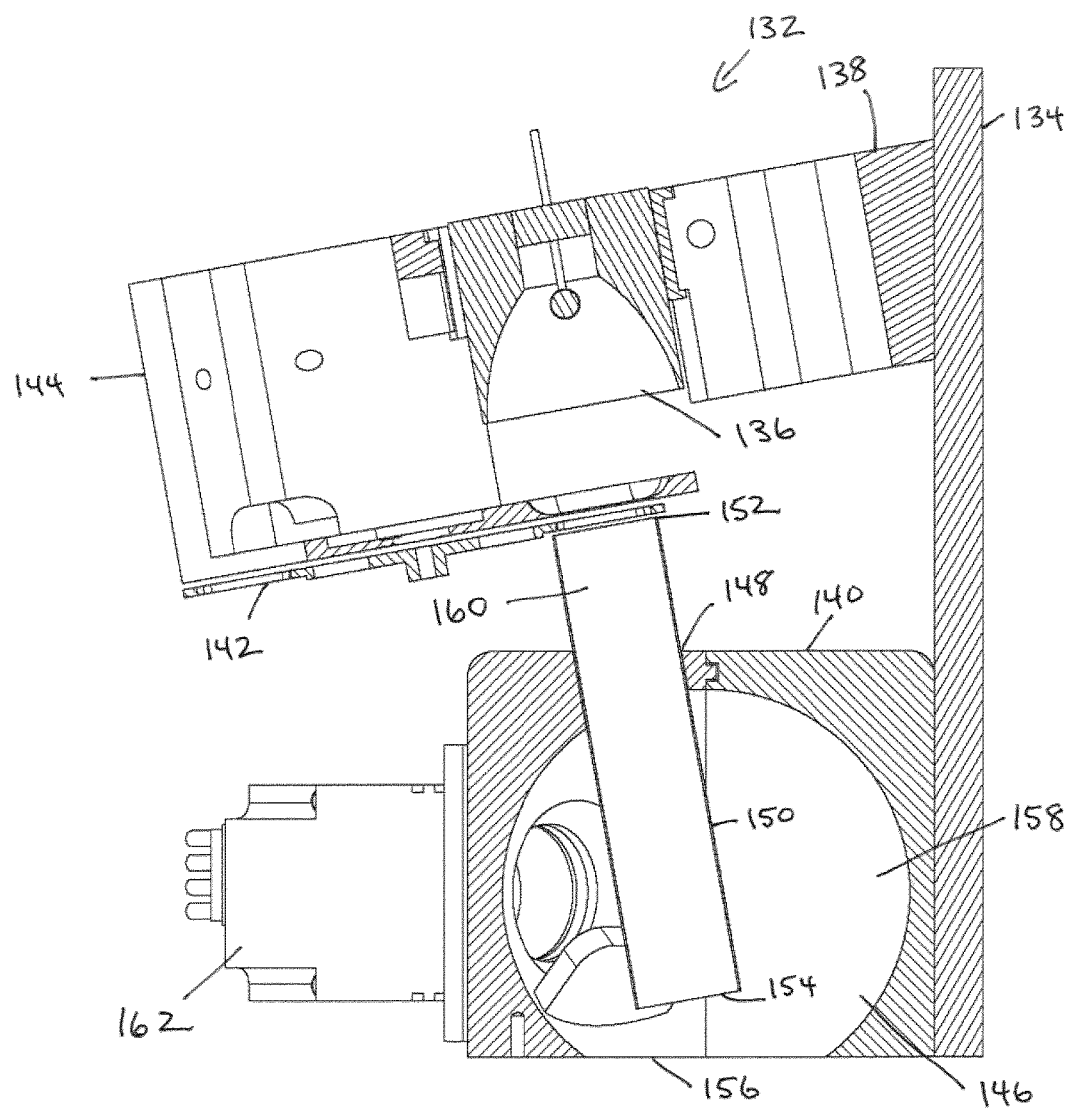
FIG. 14 is a cross-sectional side view of the system of FIG. 12.
Figure 15:
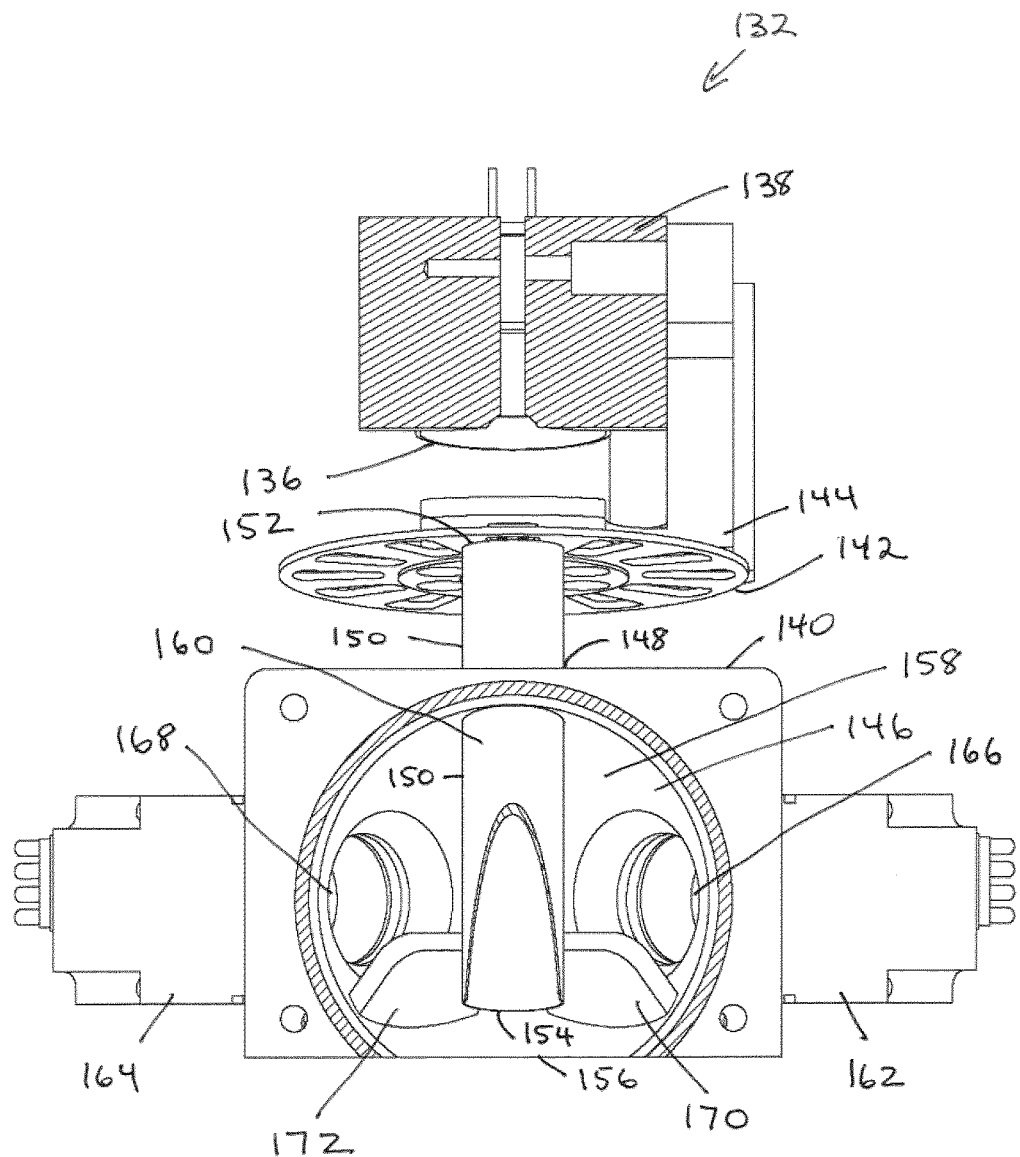
FIG. 15 is a cross-sectional rear view of the system of FIG. 12.

FIG. 12 is a perspective view of the system 132 for measuring levels of radiation reflecting from semiconductor material of the invention of FIGS. 10 and 11. System 132 is mounted over a semiconductor, photovoltaic or other wafer manufacturing line (not shown) in which the wafers 114 pass under system 132 for processing by system 132. System 132 is mounted to and supported by optical stack mount 134 or other suitable means adjacent the wafer manufacturing line. A source of infrared radiation 136 is mounted to mount 134 by source mount 138. Source 136 may be a single source of infrared radiation or a multiple source and can provide either a broadband or multiple limited band infrared wavelengths. Examples include:
 a. Thermal emitter (broadband source);
 b. Single frequency shifting laser;
 c. Multiple single wavelength lasers;
 d. Single, frequency shifting LED; and
 e. Multiple, single wavelength LEDs A modulator 142 is positioned below source 136 to modulate the radiation emitted by source 136. Modulator 142 creates a pulsed infrared signal from the source 136. Examples of modulator 142 include:
 a. An optical chopper such as spinning aperture wheel or vibrating tuning fork; and
 b. Electronic pulse control of the source Modulator 142 is connected to and supported by mount 134 by means of modulator mount 144. (Modulator 142 is described with reference to FIG. 11 as modulator 120.) The modulator 142 is a wheel 143 with alternate openings 145 and solid areas 147 and spun by motor (not shown). Modulator 142 creates a pulsed infrared signal from the source 136. Examples include an optical chopper such as spinning aperture wheel 143, or vibrating tuning fork, or electronic pulse control of the source 136.

Source 136 is modulated by optical or electrical means to provide immunity to "Background" signals that may contain energy at the target wavelengths. There are two types of background energy; constant (or DC) and pulsed (or AC). Examples of DC background energy are the temperature of the semiconductor and sunlight. By detecting the pulsed ("AC") energy, the constant energy ("DC") is eliminated from the background. Ambient lighting is an example of AC background energy as it operates from the AC mains @50 or 60 Hz. This is eliminated from target signals by ensuring the modulation frequency of source 136 is not an odd harmonic of the AC mains and then synchronizing amplifier to the modulation frequency (commonly referred to as a locked-in amplifier).

Housing 140 is positioned below source 136 and is also attached to and supported by stack mount 134. Housing 140 houses integrating sphere 146 best seen in cross-section in FIGS. 14 and 15. Integrating sphere 146 consisting of a hollow spherical cavity with its interior surface 158 covered with a diffuse reflective coating which provides a generally uniform scattering or diffusing effect on the infrared radiation reflected from the wafer 114. Infrared radiation incident on a point on the inner surface of sphere 146, by multiple scattering reflections, is distributed substantially equally to all other points within sphere 146. The effects of the original direction of radiation reflected from the wafer 114 are minimized.

Integrating Sphere 146 includes an upper or first opening 148 (FIGS. 14 and 15) in alignment with the direction of radiation emanating from source 136 through modulator 142. Source 136 is offset from the vertical (i.e. normal to the wafers 114 travelling below on the manufacturing line) by a predetermined amount, which is preferably between approximately 5-45 degrees from normal. The most preferred angle is about ten degrees from normal. The angled offset from normal acts to minimise radiation from being reflected directly back to the collimator (if present). However, the angle must also be sufficiently low to minimise leakage of incident radiation from the source 136 into the sphere without reflecting from the wafer.

Sphere 146 also includes a lower or second opening 156 generally parallel with wafers travelling below on the manufacturing line. The ratio of the lower opening 156 diameter to the inner diameter of sphere 146 is optimized to allow as much energy to be captured while also maximizing the signal strength, which can have a range of ratios between less than 1, preferably 0.6 (3 to 5). The larger the sphere 146, the weaker the signal but the more room to place components around it and the larger the aperture to capture the energy. Lower opening 156 is relatively large in comparison to upper opening 148 and in general in comparison to the diameter of sphere 146 and is positioned relatively close to the wafer 114 (about 5 mm) to ensure that as much of the reflected radiation 114 (FIG. 10) from the wafer 114 enters sphere 146.

Where source 136 is a source of un-collimated infrared radiation, a collimator is necessary to direct, focus or collimate the radiation to a specific area on the wafer 114 as it passes below system 132 and is acted on by system 132 to measure levels of radiation reflecting from the wafer 114 for use in measuring the dopant content of the wafer 114. The collimator of the present embodiment is a conduit or light pipe 150 extending through upper end 148 with inlet end 152 of light pipe 150. Light pipe 150 is adjacent to modulator 142 to capture the radiation emanating from source 136. Light pipe 150 is positioned inside sphere 146 to ensure a direct path of the radiation from source 136 onto wafer 114. Light pipe 150 is also angled from the normal with respect to the wafers 114 at the same angle from normal as the radiation emanating from source 136, that is preferable a range between about 5 degrees and 45 degrees and most preferably about 10 degrees. In order to increase the scattering and diffusion of the infrared radiation within sphere 146, the exterior surface 160 of light pipe 150 may be coated with the same or similar diffuse reflective coating as the interior surface 158 of sphere 146.

Light pipe 150 keeps the source 136 signal away from detectors 162 and 164 and helps illuminate a specific area the wafer 114 by ensuring that more of the source 136 energy is directed to that area. The outer part of the light pipe may be made of reflective material to assist in scattering reflected radiation within the sphere. As the sphere is positioned close to the wafer the radiation cannot adequately contact the wafer from outside the sphere.

A substantial part of the body of light pipe 150 extends within sphere 146, generally through the center region of sphere 146. Lower end or outlet end 154 of light pipe 150 is positioned within sphere aligned with opening 156, preferably in co-axial alignment. And preferably, the ratio of the lower opening 156 diameter to the diameter of outlet end 154 of light pipe 150 is about 2 to 1, but can have a ratio of greater than 1.5 (3 to 2 or greater) in order to get a smaller spot size on the wafer and reduce the amount of energy lost reflected back into the light pipe as well having a higher resolution spot sample on the wafer. Preferably outlet end 154 of light pipe 150 is about 6 mm from the plane defined by lower opening 156 of sphere 146.

Modulated radiation 110 (FIG. 10) from source 136 travels through light pipe 150 to exit through outlet 154 and then opening 156 to strike a wafer 114 travelling on the manufacturing line below. Radiation 110 strikes the wafer 114 at an angle determined by the angled positions of source 136 and light pipe 150 and is reflected by the wafer 114 at a return angle, as best seen in an exemplary manner in FIG. 10. Primarily due to the angle from normal most of the reflected radiation 112 (FIG. 10) travels upwardly into the sphere avoiding outlet end 154 of light pipe 150, thereby minimising specular reflection interfering with the radiation from source 136.

As an example, the diameter of lower opening 156 of sphere 146 is about 3 cm, the inner diameter through the center of sphere 146 is about 5 cm, and the diameter of outlet end 154 of light pipe 150 is about 1.3 cm.

Sphere 146 includes a pair of infrared radiation detectors 162 and 164 positioned to measure the amount of radiation within sphere 146 contacting each detector 162 and 164. (Detectors 162 and 164 are described with reference to FIG. 11 as detectors 124 and 126 and with reference to FIG. 4 as detectors 20 and 22.) Band pass filters 166 and 168 are positioned between respective detectors 162 and 164 and the interior of sphere 146.

Band pass filter 166, or first band pass filter, (which may also be an edge pass filter—not shown) is positioned to receive a first portion of the received radiation reflected from the wafer 114 or material in sphere 146 and is configured to pass a limited wavelength band of infrared radiation centered at a selected wavelength of the infrared radiation source 136 through filter 166 to detector 124. Band pass filter 168, or second band pass filter, (which may also be an edge pass filter—not shown) is positioned to receive a second portion of the received radiation reflected from the wafer 114 or material and is configured to pass a limited wavelength band of infrared radiation centered at a selected wavelength of the infrared radiation source 136 through the filter 168. The limited wavelength band that is passed by filter 168 is different as compared to the limited wavelength band passed by filter 166.

In a preferred embodiment, and when band pass filters 166 and 168 are employed, band pass filters 166 and 168 are preferably centred at about 1.6 microns and 5.4 microns. In general the pass bands are chosen such that the amplitudes of reflection at one or both are dominated by free carrier absorption.

Integrating sphere 146 includes a pair of inner baffles 170 and 172 positioned within sphere 146 to prevent direct reflected energy 114 from contacting detectors 162 and 164, respectively. All energy 112 entering sphere 136 through opening 156 should have been diffused or scattered in the integrating sphere 146 as much as is possible before hitting a detector 162 or 164.

Sphere 146 acts to equalize the energy within the sphere due to reflection and scattering within sphere 146. Any original directional factors of the reflected radiation from the wafer 114 is also removed by that same action. As a result the two detectors 162 and 164 receive approximately the same average level of reflected energy 112 (FIG. 10). This prevents uneven levels of radiation at detectors 162 and 164 caused by different surface characteristics at various regions of the wafers 114. The amount of energy 112 emitting from the wafer 114 at the target wavelengths is a function of the concentration of the dopant of wafer 114 to be detected by system 132.

Signals from detectors 162 and 164 travel to demodulator 128 (FIG. 11) which is in synchronisation with modulator 120 (FIG. 11) or modulator 142 (FIGS. 12-15), for demodulation. The demodulated signal then travels to the signal processor 130 (FIG. 11) for processing, as discussed more fully above. The synchronising can be undertaken by a signal amplifier synchronized to the modulation frequency (commonly referred to as a locked-in amplifier).

Figure 16:
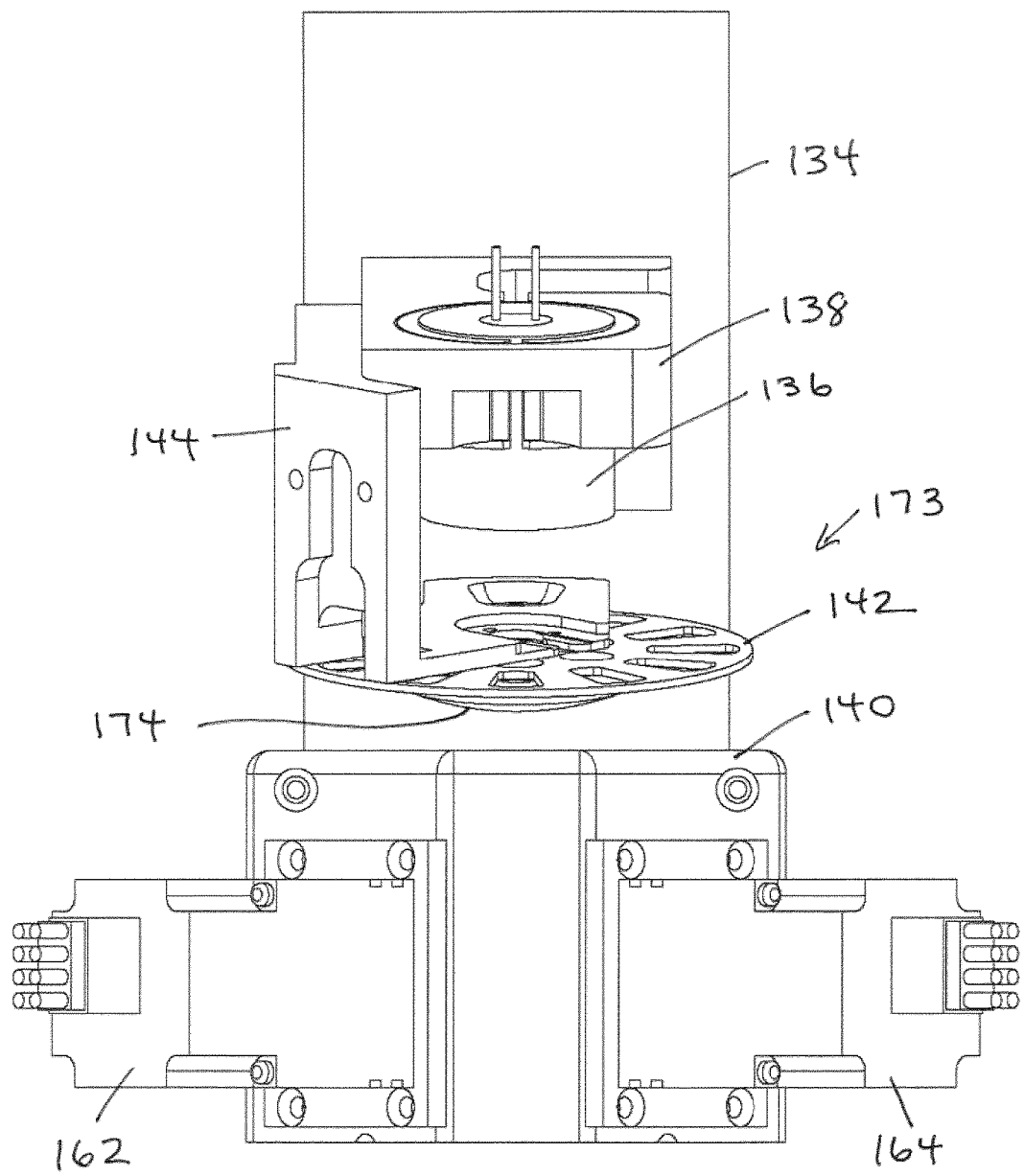
FIG. 16 is a front view of an alternate system with a collimated infrared source and without a conduit or light pipe.
Figure 17:
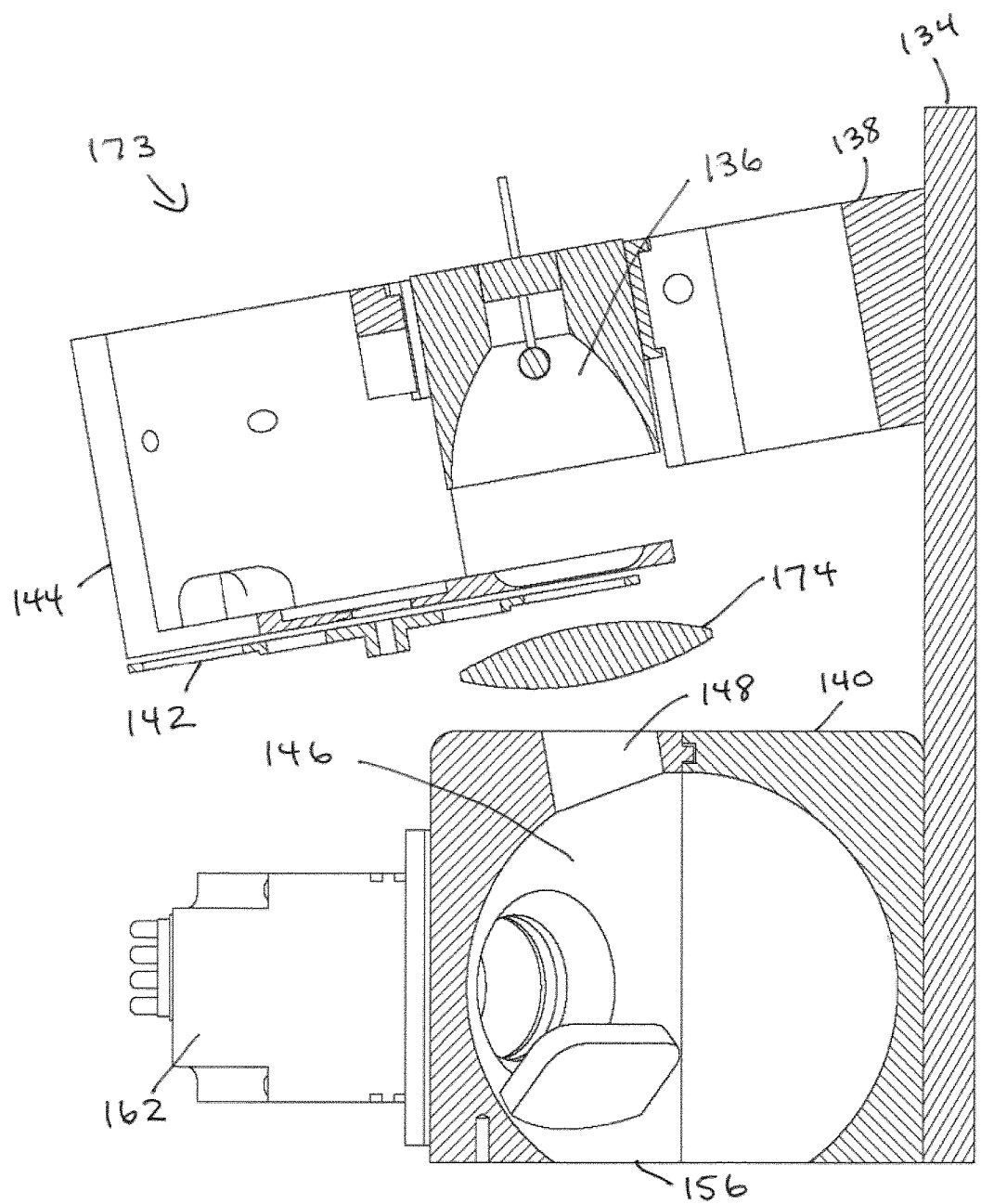
FIG. 17 is a cross-sectional side view of the system of FIG. 16.

An alternate embodiment is discussed with reference to FIGS. 16 and 17. This embodiment is the same as the embodiment discussed with reference to FIGS. 10 to 15 above, except that system 173 source 136 is a source of collimated infrared radiation such as an infrared laser or LED thereby foregoing the need for a collimator such as light pipe 150. Instead lens 174 is positioned between collimated source 136 and upper or first opening 148, below modulator 142.

Source 136 is offset from the vertical (i.e. normal to the wafers 114 travelling below on the manufacturing line) by a predetermined amount, which is preferably between approximately 5-45 degrees from normal. The most preferred angle is about ten degrees from normal. The angled offset from normal acts to minimise specular reflection, which is important to prevent reflected radiation from the wafer 114 from interfering with the radiation from source 136. Source 136 radiation is focussed by lens 174 and travels through sphere 146 to exit opening 156 at the same angle from the normal as the radiation from source 136. The radiation then impacts a part of the wafer 114 at the said angle, as depicted in FIG. 10. Reflected radiation enters the sphere 146 through opening 156 to be reflected within sphere 146 multiple time and then to impact one of filters 166 and 168 to be filtered based on the predetermined pass band of filters 166 and 168 before impacting associated detectors 162 and 164, all as previously discussed with reference to the filters 166, 168 and detectors 162, 164 of the prior embodiment.

From the foregoing, it will be appreciated that specific embodiments of the invention have been described herein for purposes of illustration, but that various modifications may be made without deviating from the spirit and scope of the various embodiments of the invention. Further, while various advantages associated with certain embodiments of the invention have been described above in the context of those embodiments, other embodiments may also exhibit such advantages, and not all embodiments need necessarily exhibit such advantages to fall within the scope of the invention.

I claim:

1. A system for measuring levels of radiation reflected from semiconductor material for use in measuring the dopant content of the material, comprising:
 a) an infrared radiation source;
 b) a modulator for modulating the radiation from the infrared radiation source;
 c) an integrating sphere having a first opening for receiving the modulated radiation from the source and a second opening for receiving radiation reflected from the material, the sphere configured to scatter the received radiation reflected from the material within the sphere;
 d) a light pipe extending through the first opening into the integrating sphere and towards the second opening of the sphere, the light pipe configured to direct the radiation from the infrared radiation source through the sphere to impact the material at an angle in a range between about 5 degrees and 45 degrees from the normal with reference to the material, the angle sufficient to minimise radiation from being reflected directly back into the light pipe and also to minimise radiation entering the sphere before reflecting from the material;
 e) a first baffle positioned within the sphere to prevent the received radiation reflected from the material from travelling to a first band pass or edge pass filter without first scattering within the sphere;
 f) a second baffle positioned within the sphere to prevent the received radiation reflected from the material from travelling to a second band pass or edge pass filter without first scattering within the sphere;
 g) the first band pass or edge pass filter positioned to receive a first portion of the received radiation reflected from the material, the first band pass or edge pass filter configured to pass a limited wavelength band of infrared radiation from within the overall spectrum emitted by the infrared radiation source through the first filter;
 h) the second band pass or edge pass filter positioned to receive a second portion of the received radiation reflected from the material, the second band pass or edge pass filter configured to pass a limited wavelength band of infrared radiation from within the overall spectrum emitted by the infrared radiation source through the second filter, wherein the limited wavelength band that is passed by the second filter is different as compared to the limited wavelength band passed by the first filter;
 i) a first radiation detector positioned to receive the radiation that passes the first filter and configured to determine a first level of energy; and
 j) a second radiation detector positioned to receive the radiation that passes the second filter and configured to determine a second level of energy.

2. The system of claim 1 wherein the angle from the normal is about ten degrees.

3. The system of claim 1 wherein the angle from the normal is sufficiently low to minimize leakage of modulated radiation from the source into the sphere without reflecting from the material.

4. The system of claim 1 wherein the light pipe has an inlet end that receives radiation from the infrared radiation source and an outlet end that emits the radiation at or near the second opening of the sphere.

5. The system of claim 4 wherein the light pipe comprises an outer surface configured to enhance reflection of the radiation within the sphere of the received radiation reflected from the material.

6. The system of claim 4 wherein the second opening and the outlet end of the light pipe are in co-axial alignment.

7. The system of claim 4 wherein the diameter of the second opening of the sphere is larger than the diameter of the outlet end of the light pipe.

8. The system of claim 4 wherein the second opening of the sphere is about 3 cm in diameter and the sphere is about 5 cm in its inner diameter.

9. The system of claim 8 wherein the diameter of the outlet end of the light pipe is about 1.3 cm.

10. The system of claim 4 wherein the ratio of the second opening diameter to the diameter of the light pipe downstream opening is about 2 to 1.

11. The system of claim 4 wherein the ratio of the second opening diameter to the diameter of the outlet end of the light pipe is equal to or greater than 1.5 to 1.

12. The system of claim 4 wherein the outlet end of the light pipe is about 6 mm from the plane defined by the second opening of the sphere.

13. The system of claim 1 wherein the light pipe extends lengthwise through the centre of the sphere for substantially the entire diameter of the sphere.

14. The system of claim 1 wherein the modulated radiation from the source exits the sphere to impact the material through the second opening.

15. The system of claim 1 wherein the first and second baffles are configured to block substantially the same degree of received radiation reflected from the material.

16. The system of claim 1 wherein the sphere comprises an internal surface configured to enhance reflection within the sphere of the received radiation reflected from the material.

17. The system of claim 1 wherein the second opening is positioned a distance from the material to cause substantially all of the radiation reflected from the material to enter the sphere irrespective of surface variations of the material.

18. The system of claim 17 wherein the second opening is positioned about 5 mm from the material.

19. The system of claim 1 wherein the modulator is selected from the group:
   a) a modulator using a chopping wheel;
   b) a modulator using pulse modulation of the source; and
   c) a modulator using frequency modulation of the source.

20. The system of claim 1 wherein the radiation source is either: a) a multi-wavelength infrared laser, b) more than one infrared laser each at a different wavelength, c) one or more infrared light emitting diodes, or d) a source of broadband infrared radiation.

21. The system of claim 1 wherein the pass bands for both the first filter and second filter are longer than 1 micrometer.

22. The system of claim 1 wherein the pass bands are selected such that the amplitudes of reflection at one or both are dominated by free carrier absorption.

23. The system of claim 1 wherein the ratio of the second opening diameter to the inner diameter of the sphere is about 3 to 5.

24. The system of claim 1 further comprising an amplifier for amplifying the determinations of first and second levels of energy, the amplifier synchronized to the radiation modulation frequency.

* * * * *